United States Patent [19]

Kluger et al.

[11] Patent Number: 5,250,665

[45] Date of Patent: Oct. 5, 1993

[54] SPECIFICALLY β-β CROSS-LINKED HEMOGLOBINS AND METHOD OF PREPARATION

[75] Inventors: Ronald Kluger, Don Mills; Jolanta Wodzinska, Scarborough, both of Canada

[73] Assignee: The University of Toronto Innovations Foundation, Toronto, Canada

[21] Appl. No.: 746,372

[22] Filed: Aug. 16, 1991

Related U.S. Application Data

[63] Continuation-in-part of Ser. No. 707,350, May 31, 1991, abandoned.

[51] Int. Cl.[5] .................. C07C 103/52; C07K 13/00; A61K 35/14
[52] U.S. Cl. .................. 530/385; 530/402; 530/410
[58] Field of Search .................. 530/385, 402, 410; 514/6

[56] References Cited

U.S. PATENT DOCUMENTS

| | | | |
|---|---|---|---|
| 2,648,696 | 8/1953 | Whetstone | 514/6 |
| 4,001,200 | 1/1977 | Bonsen et al. | 530/385 |
| 4,001,401 | 1/1977 | Bonsen et al. | 514/6 |
| 4,053,590 | 10/1977 | Bonsen et al. | 514/6 |
| 4,061,736 | 12/1977 | Morris et al. | 514/6 |
| 4,473,496 | 9/1984 | Scannon | 530/385 |
| 4,529,719 | 7/1985 | Tye | 514/6 |
| 4,584,130 | 4/1986 | Bucci et al. | |
| 4,598,064 | 7/1986 | Walder | 530/385 |
| 4,600,531 | 7/1986 | Walder | 530/385 |
| 4,670,417 | 6/1987 | Iwasaki | 514/6 |
| 4,777,244 | 10/1988 | Bonhard et al. | 530/385 |
| 4,857,636 | 8/1989 | Hsia | 530/385 |

FOREIGN PATENT DOCUMENTS

0361720 of 0000 European Pat. Off.
8404242 11/1984 European Pat. Off. .......... 530/385

OTHER PUBLICATIONS

Hemoglobin Covalently Bridged Across the Polyphosphate Binding Site, Benesch et al. Biochem., Biophys Res. Comm. vol. 63, No. 4, 1975.
Kluger and Tsui J. Org. Chem. 45:2723, 1980.
Ueno et al Arch. Biochem. Biophys. 244:795, 1986.
Ueno et al J. Biol. Chem. 264:12344, 1989.
Kiuger and Tsui Biochem. Cell. Biol. 64:434, 1986.
Snyder et al. Proc. Natl. Acad. Sci. U.S.A. 84:7280, 1987.
Chatterjee et al. J. Biol. Chem. 261:9929, 1986.
Kavanaugh et al. Haem. Proc. Int. Meeting London 1986 Acta 78:99, 1986.
Kavanaugh et al. Biochem. 27:1804, 1988.
Benesch and Benesch Methods in Enzymol. 76:147, 1981.
Benesch and Kwong Biochem. Biophys. Res. Comm. 156:9, 1988.
Yang and Olsen, Biochem, Biophys. Res. Comm. 163:733, 1989.
Kluger et al. J. Org. Chem. 55:2864, 1990.
Jones et al. Biomaterails, Artificial Cells and Artifical Organs 17:643, 1989.
Manning et al. Proc. Natl. Acad. Sci. 88:3329, 1991.
Yang and Olsen, Biochem, Biophys. Res. Comm. 174:518, 1991.
Benesch et al., Biochemistry 11:3576, 1972.
Pool, Science 250:1655, 1990.

*Primary Examiner*—Michael G. Wityshyn
*Assistant Examiner*—P. Lynn Touzeau
*Attorney, Agent, or Firm*—Bereskin & Parr

[57] ABSTRACT

A modified hemoglobin comprising hemoglobin which is cross-linked with a cross-linking reagent. The cross-linking reagent is selected such that the β-chains are cross-linked within the 2,3-diphosphoglycerate binding site and the linkage distance between the β-chains is between about 5 to 9 angstroms. A method of preparing the modified hemoglobin and its use as a blood substitute or a plasma expander are also described.

36 Claims, 21 Drawing Sheets

SPECIFICALLY β-β CROSS-LINKED HEMOGLOBINS AND METHOD OF PREPARATION

This is a Continuation-In-Part of U.S. patent application No. 07/707,350 filed May 31, 1991, now abandoned.

FIELD OF THE INVENTION

The present invention relates to a modified hemoglobin, a method of preparing the modified hemoglobin, and its use as a blood substitute and blood plasma expander.

BACKGROUND OF THE INVENTION

The potential use of modified hemoglobin as a substitute for red blood cells in transfusions is widely documented to fill a critical need in medical therapeutics. Circulating red blood cells serve to deliver oxygen to tissues. A decrease in red blood cells as the result of loss of blood, causes serious and irreversible damage to organs. Large losses are life-threatening. Red blood cells present problems with respect to administration (typing), storage, and infection (AIDS, hepatitis). Thus, a product that would replace red blood cells in transfusions is widely sought.

Hemoglobin is the oxygen-carrying component of the red cell. Unmodified hemoglobin is a tetrameric assembly of protein components consisting of two sets of paired subunits, each with a heme prosthetic group to which oxygen binds. Outside the cell its properties are such that it cannot be used as a replacement for the cellular material. The unmodified material dissociates into dimeric units outside the cell. The dissociated form is not a useful substance and causes problems in the kidney. Thus, a cross-link is necessary to hold the subunits together. Another problem is that hemoglobin will deliver oxygen to cells if it is first oxygenated and if its affinity for oxygen is lower than that of the target cell.

As naturally occurring materials in humans and animals, hemoglobins are not expected to be treated as a foreign substance by the immune system. Thus, if the properties of hemoglobin can be adjusted by chemical modification to introduce properties necessary for hemoglobin to be used as a red cell substitute, an important product will result.

In the red blood cell, a high endogenous 2,3-diphosphoglycerate (DPG) binds to hemoglobin and induces hemoglobin to exist in a state that has a sufficiently low affinity for oxygen to transfer oxygen to the tissues. In order to keep the low affinity state of hemoglobin, it is desirable to permanently introduce an effect similar to that of DPG since the DPG concentration in the circulation is very low. The cooperative binding of oxygen (as indicated by Hill coefficient) should be maintained in order to have efficient transfer occur. The chemical modifications should also not be reversible. Further, modifications should be readily and specifically performed so that the product can be well-characterized and conveniently prepared.

Methyl acetyl phosphate originally synthesized as a site-specific reagent for hydroxybutyrate dehydrogenase (Kluger and Tsui (1980) J. Org. Chem. 45, 2723) has been reported to have an affinity for the binding site for 2,3-diphosphoglycerate in hemoglobin (Ueno et al., Archives Of Biochemistry And Biophysics, Vol. 244, No. 2, 795 (1986) and Ueno et al., The Journal of Biological Chemistry, Vol. 264, No.21, 12344 (1989)). It has been documented that three residues in or near this cleft between the beta-chains are acetylated by this reagent. The acetylation of Val-1, Lys-82 and Lys-144 and the absence of the acetylation of any of the amino groups of the alpha-chain indicate the specificity of methyl acetyl phosphate in its reaction with hemoglobin (Ueno et al., Archives Of Biochemistry And Biophysics, Vol. 244, No. 2, 795 (1986). It has further been documented that methyl acetyl phosphate and other monoesters of acyl phosphates may be used as acetylating agents for nucleophilic groups on proteins (Kluger, R. and Tsui, W. C., Cell Biol., Vol.64, 434 (1986)).

Many cross-linking reagents have been used in an attempt to produce a modified hemoglobin with oxygen transport properties similar to whole blood. The bifunctional analog 2-nor-2-formyl-pyridoxal 5'-phosphate provides a means of cross-linking the hemoglobin tetramer between the beta-subunits and has been reported to reduce oxygen affinity (Benesch et al., Biochem. Biophys. Res. Comm. 63, 1123-1129 (1975), J. Mol. Biol. 115, 627-642 (1977), Proc. Natl. Acad. Sci. U.S.A. 81, 2941-2943 (1984)). However, the cross-linking reagent is difficult to synthesize.

Under deoxygenated conditions, bis(3,5-dibromosalicyl) fumarate reacts with hemoglobin selectively to cross-link the alpha subunits between Lys-$\alpha_1$99 and Lys-$\alpha_2$99. The oxygen transport characteristics of this product were found to be similar to whole blood (Snyder et al., Proc. Natl. Acad. Sci. U.S.A. 84, 7280-7284 (1987) and Chatterjee et al., J. Biol. Chem., Vol. 261, No.21, 9929-9937 (1986).

U.S. Pat. No. 4,584,130 to Bucci and Fronticelli-Bucci describes a stable cross-linked, stroma-free hemoglobin, having a physiologically acceptable oxygen affinity. The cross-linking reagents were produced from one of two starting compounds, 2,2'-sulfonyl-bis-acetonitrite or 2,2'-sulfonyl-bis-acetate, which were reacted with sodium borohydride in a nitrogen atmosphere. To the product of this reaction was added, for example methyl chloroformate or 1,1'-sulfonyl-bis-imidazole to produce methyl 2,2'sulfonyl-bis-cyanoacetate and 2,2'-sulfonyl-2,2'imidazole-N-sulfonyl-bis-acetonitrile respectively. These compounds cross-link hemoglobin by binding preferentially, but not exclusively, in the 2,3-diphosphoglycerate (DPG) binding site. Reactions outside the DPG-binding site produce intermolecular cross-links.

Walder U.S. Pat. No. 4,600,531 describes a cross-linked stroma-free hemoglobin product suitable for use as a blood substitute and plasma expander. Walder discloses the use of phenyl esters, preferably bis (3,5-dibromosalicyl) fumarate, to cross-link hemoglobin between the two alpha-99 lysyl residues. Deoxyhemoglobin is reacted with the cross-linker in the presence of an added polyanion, such as inositol hexaphosphate, to block competing reactions at other sites of the protein, such as the DPG-binding site. Walder also discloses the reaction of oxyhemoglobin with mono (3,5-dibromosalicyl) fumarate to introduce a negatively charged carboxylate within the DPG-binding site.

SUMMARY OF THE INVENTION

The present invention provides a modified hemoglobin comprising hemoglobin which is cross-linked with a cross-linking reagent, said cross-linking reagent being selected such that the β-chains are cross-linked within the 2,3-diphosphoglycerate binding site and the distance between the β-chains is between about 5 to 9 angstroms.

Preferably, the cross-linking reagent is selected such that the β-chains are cross-linked between the epsilon amino group of lysine-82 of one chain and the alpha amino group of valine-1 of the other chain and the distance between the β-chains is about 7 angstroms.

In accordance with one embodiment of the invention a modified hemoglobin is provided which is obtained by cross-linking hemoglobin with a cross-linking reagent comprising an aromatic- or aliphatic-derived acyl material having at least two anionic leaving groups each anionic leaving group being adjacent to an electrophile group, said cross-linking reagent being selected such that a first electrophile group reacts covalently with the epsilon group lysine 82 of a first β chain of said hemoglobin and a second electrophile group reacts covalently with the alpha amino group valine-1 of a second β chain of said modified hemoglobin whereby said hemoglobin is intramolecularly cross-linked between said beta chains such that the distance between the β chains at said cross-link is between about 5 to 9 angstroms.

Preferably, the cross-linking reagent comprises an aromatic- or aliphatic-derived acyl material having at least three anionic leaving groups and wherein a third electrophile group reacts covalently with the epsilon group lysine 82 of said second β chain of said hemoglobin or the alpha amino group valine-1 of said first β chain of said hemoglobin.

The cross-linking reagent may comprise an aromatic- or aliphatic-derived acyl material having at least four anionic leaving groups and a fourth electrophile group may react covalently with the alpha amino group va-line-1 of said first β chain of said hemoglobin in the case where the third electrophile group reacts covalently with the epsilon group lysine 82 of said second β chain of said hemoglobin.

The cross-linking reagent may also comprise an aromatic- or aliphatic-derived acyl material having at least four anionic leaving groups and a fourth electrophile group may react covalently with the epsilon group lysine 82 of said second β chain of said hemoglobin in the case where the third electrophile group reacts covalently with the alpha amino group valine-1 of said first β chain of said hemoglobin.

In accordance with a preferred embodiment of the invention the cross-linking reagent is a compound of the formula I:

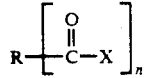

wherein R is a linear or branched alkyl, alkenyl, phenyl, diphenylalkenyl, benzyl, napthyl, phenylalkyl, phenylalkenyl or diphenylalkyl, preferably phenyl; X is an anionic leaving group and n is an integer, preferably between 2 and 4, and most preferably 3.

An "electrophile group" is well known in the art and can be a molecule or ion that can furnish an electron pair. Electrophiles can combine with another molecule or ion by forming a covalent bond with two electrons from the second molecule or ion.

An "anionic leaving group" is well known in the art and can be an atom or group of atoms which can easily leave as a relatively stable, weakly basic group. Examples of anionic leaving groups are, phosphate, alkanesulfonate, alkylsulfate, asalicylate or hydroxyl, preferably a group of the formula II

wherein one of $R^1$ and $R^2$ represents $-O^-$ and the other of $R^1$ and $R^2$ represents a linear or branched alkyl group having up to 4 carbon atoms, benzyl or phenyl.

Particularly preferred cross-linking reagents are the tris acyl (methyl phosphate) ester of 1,3,5-benzene-tricarboxylic acid, the 3,5-tris dibromo acetyl salicylate of 1,3,5-benzene-tricarboxylic acid, isophthalic bis (methyl phosphate), cis and trans cyclohexyl 1,3,5-tricarboxylic acid tris (sodium methyl phosphate), or the dibromosalicylate of isophthalic acid.

In an embodiment of the present invention a specifically intramolecularly beta-beta cross-linked hemoglobin is provided that is produced in commercially significant yields. The cross-link occurs in the 2,3diphosphoglycerate (DPG) binding site. Trifunctional reagents which readily accomplish this modification are introduced. The triple-headed reagent has an advantage over bifunctional reagents in that the third reactive functionality enhances the affinity of the reagent for the DPG binding site and increases the probability of the specific cross-linking reaction. One of the products these trifunctional cross-linkers produce is a triply cross-linked hemoglobin. Cross-linked products from these reagents have oxygen binding properties and cooperativity properties which make them suitable for use as a red blood cell substitute.

The invention also provides a method of preparing a modified hemoglobin as hereinbefore described comprising cross-linking hemoglobin with a cross-linking reagent, said cross-linking reagent being selected such that the β-chains are cross-linked within the 2,3-diphosphoglycerate binding site and the distance between the β-chains is between about 5 to 9 angstroms, and purifying the resulting cross-linked hemoglobin. Preferably the modified hemoglobin is prepared using deoxyhemoglobin or oxyhemoglobin.

In accordance with an embodiment of the invention a method of preparing a modified hemoglobin is provided comprising (a) cross-linking hemoglobin with a cross-linking reagent comprising an aromatic- or aliphatic-derived acyl material having at least two anionic leaving groups each anionic leaving group being adjacent to an electrophile group, said cross-linking reagent being selected such that a first electrophile group reacts covalently with the epsilon group lysine 82 of a first β chain of said hemoglobin and a second electrophile group reacts covalently with the alpha amino group valine-1 of a second β chain of said modified hemoglobin whereby said hemoglobin is intramolecularly cross-linked between said beta chains such that the distance between the β chains at said cross-link is between about 5 to 9 angstroms; and (b) purifying the resulting cross-linked hemoglobin. Preferably the hemoglobin is deoxyhemoglobin or oxyhemoglobin. The hemoglobin may be selected from the group consisting of human, equine, porcine, ovine, bovine, simian and fish hemoglobin.

The invention further relates to the use of a modified hemoglobin as hereinbefore described as a blood substitute, red cell substitute, oxygen transfer agent and carrier, or a plasma expander.

BRIEF DESCRIPTION OF THE DRAWINGS

The invention will be better understood with reference to the drawings in which.

DETAILED DESCRIPTION OF THE INVENTION

The present invention consists of specifically modified hemoglobins which are readily prepared and which have the properties necessary to be used as red cell substitutes. In particular, the present inventors have found that hemoglobin containing a covalent connection between the epsilon amino group of lysine-82 of one beta subunit to the alpha amino group of valine-1 of the other beta subunit of hemoglobin possesses the properties desired. This is a cross-link in the DPG binding site. Furthermore, the present inventors have found that the length of cross-link may be important in maintaining the low oxygen affinity state and cooperativity. Table I shows the bridging distances for selected cross-linking reagents and the distances between $\beta 1\text{Val-NH}_2$ and $\beta 82\text{-lys-NH}_2$ in oxy and deoxyhemoglobin. The length of the cross-linking agents is not identical to the distances between the $\beta$ chains, at the linkage sites of the unmodified hemoglobins. For example, isophthaloyl bis (methyl phosphate) has a linkage distance of 7.3 angstroms and cross-links deoxyhemoglobin between $\beta 1$ and $82\beta$. In unmodified deoxyhemoglobin the distance between $\beta 1$ and $82\beta$ is 11.5 angstroms.

The derivative containing an isophthalic linkage between amino groups, or another linkage of similar geometry, has been found to yield an efficiently functioning product. In particular the reagent 1,3,5-benzene tricarboxylic acid tris (methyl phosphate) provides a straightforward means to introduce the necessary structure in high yield.

It is believed that the reaction occurs initially at lys-82, based on the known higher degree of reactivity of this residue. The reagent then more slowly reacts with val-1 of the other subunit to produce the desired cross-link. However, it may also add internally to val-1 of the same subunit. Since another reacting group remains, it can still generate the necessary cross-link unless a second molecule of reagent has reacted with the other subunit, in which case cross-linking is prevented. However, the use of the infusion reaction conditions, described in Example 5, minimizes the likelihood of a second molecule of reagent reacting with the other subunit. This analysis is consistent with the data shown in Table II which shows that the cross-linked derivatives contain at least one modified lys-82. Those which are not cross-linked do not contain an internal 1-82 link. Therefore, reagents that generate linkages comparable in dimensions to the relationship of the carboxyl groups of isophthalic acid should produce hemoglobins with the appropriate properties.

Measurements from molecular modelling calculations indicate that a distance between carboxyl groups of between about 5 to 9 angstroms will provide material that will be useful, preferably the distance between carboxyl groups is about 7 angstroms. The reagent used to produce the cross-link should ideally provide the necessary specificity for reaction.

Figure 1:
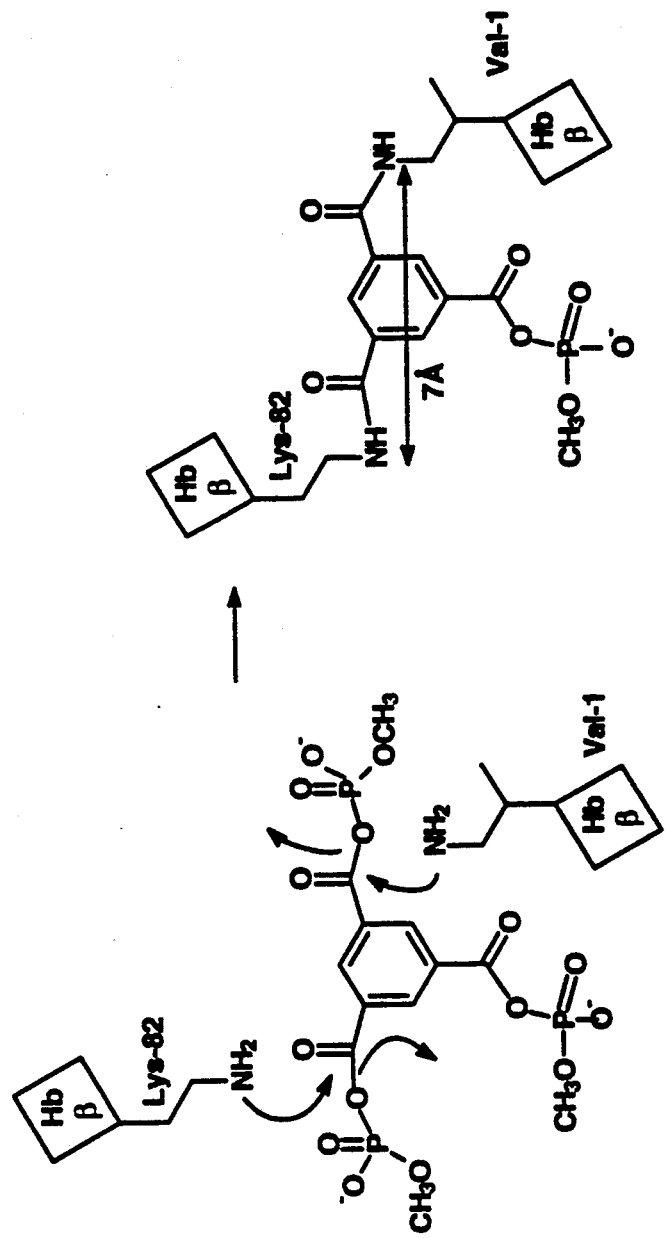
FIG. 1 is a chemical reaction scheme for the modification of hemoglobin by specific reagents.

A new class of cross-linking compounds, acyl bis(-sodium methyl phosphates) described in copending U.S. patent application Ser. No. 493,524, which is incorporated herein by reference are useful as cross-linking reagents in the present invention. Trifunctional cross-linkers such as acyl tris(sodium methyl phosphates) are particularly useful in the present invention. The tris acyl (methyl phosphate) ester of 1,3,5-benzene-tricarboxylic acid is a preferred reagent. FIG. 1 is a schematic diagram showing the reaction of the 1,3,5-benzene compound with hemoglobin in the DPG binding cleft. The introduction of the third reactive functional group not only statistically increases the probability of the reaction with amino groups of hemoglobin but also increases the affinity of the highly anionic reagent to the DPG binding site. All three acyl phosphate groups can react with hemoglobin producing triply cross-linked species. If two of the three groups react to produce a linkage between the epsilon group lysine-82 of one chain and the alpha amino group of valine-1 of the other chain, the resulting product is also useful.

The acyl bis(sodium methyl phosphate) cross-linking reagents can be prepared by the methods described in copending U.S. application Ser. No. 493,524, the teachings of which are incorporated herein by reference. For example, reagents can be prepared in two steps starting from di- or tricarboxylic acid di- or trichlorides. Acyl bis and tris(dimethyl phosphates) can be prepared in the reaction of acid chloride and sodium dimethyl phosphate in tetrahydrofuran. Acyl bis and tris(sodium methyl phosphates) can be prepared in the reaction of acyl bis or tris(dimethyl phosphates) and sodium iodide in dry acetone.

Other reagents which are expected to give similar products in the cross-linking reaction are other derivatives of di- and tricarboxylic acids containing negative charges at each end. The tris dibromo acetyl salicylate of 1,3,5-benzene-tricarboxylic acid, isophthalic bis (methyl phosphate), the dibromosalicylate of isophthalic acid and similarly sized aromatic- and aliphatic-derived acyl materials with anionic leaving groups should also give suitable products. The tris (3,5-dibromosalicylate) ester of 1,3,5-benzene tricarboxylic acid may be prepared from the reaction of 1,3,5-benzene tricarboxylic acid chloride with three equivalents of 3,5-dibromosalicylic acid and three equivalents of a tertiary amine in benzene. The preferred cross-linking reagent is 1,3,5-benzene tricarboxylic acid tris(sodium methyl phosphate). It effectively cross-links hemoglobin producing a mixture of cross-linked hemoglobins in 60–75% yield under the conditions described below. The components of the mixture are shown in Table II.

The modified hemoglobins of the invention have been found to have oxygen binding properties in the physiologically acceptable range necessary for providing oxygen to tissues.

As hereinbefore mentioned the present invention also relates to a method of preparing a modified hemoglobin comprising cross-linking hemoglobin with a cross-linking reagent. The cross-linking reagent is selected such that the β-chains are cross-linked within the 2,3-diphosphoglycerate binding site and the linkage distance between the β-chains is between about 5 to 9 angstroms. The resulting cross-linked hemoglobin is purified using methods known in the literature.

Liganded (oxy-, carboxy-, carbonmonoxy-, or derivatives) and unliganded (deoxy-) hemoglobin may be used in the method of the invention. The hemoglobin which may be cross-linked may be human, equine, porcine, ovine, bovine, simian or fish hemoglobin.

Suitable cross-linking reagents which may be used in the method of the invention are described above and include aromatic- or aliphatic-derived acyl materials with anionic leaving groups, for example, reagents that generate linkages comparable in dimensions to the relationship of the carboxyl groups of isophthalic acid. Preferred cross-linking reagents are the tris acyl (methyl phosphate) ester of 1,3,5-benzenetricarboxylic acid, cis or trans 1,3,5-cyclohexyl tricarboxylic acid methyl phosphate, the tris dibromo acetyl salicylate of 1,3,5-benzene-tricarboxylic acid, isophthalic bis (methyl phosphate), or the dibromosalicylate of isophthalic acid.

The reaction of the hemoglobin with the cross-linking agent may occur at a temperature of from about 0° C. to 60° C. The pH of the reaction can vary from about 5.5 to about 10 with the reaction occurring in a buffer, typically Bis-Tris, Tris-HCl or HEPES buffer. The reaction time may vary but generally a sufficient degree of cross-linking occurs within 3 days. The modified hemoglobin may then be separated from the unreacted hemoglobin and other impurities using techniques known in the literature.

The cross-linking reagents used in the method of the invention are highly specific for selected groups on the hemoglobin molecule as hereinbefore mentioned which results in a high yield of the desired modified hemoglobin product. It may not be necessary to use a purified hemoglobin preparation, for example stroma free hemoglobin, to prepare the modified hemoglobin of the invention due to the specificity of the cross-linking reagents described herein for the DPG cleft of hemoglobin. Further, the cross-linking reagents described herein are covalently linked in the DPG cleft and the reagent at the linkage sites has a net neutral or negative charge.

In a preferred method of the invention deoxyhemoglobin free of 2,3-diphosphoglycerate is used to produce modified hemoglobins cross-linked between beta chains. The reaction with the cross-linking agent and the hemoglobin can occur at a temperature of from 20° C. to 60° C. The pH of the reaction can vary from 6 to 8. The reaction can be carried out in aqueous solution of buffers, including Bis-Tris-HCl, Tris-HCl, and HEPES. The concentration of buffer is typically 0.1M. The ratio of the cross-linking reagent to hemoglobin can vary from 2:1 to 10:1, preferably 2:1. The time of the reaction is up to 3 days at room temperature, or 3 hours at 60° C., for a sufficient degree of cross-linking to occur. The cross-linking reagent is introduced into the reaction vessel anaerobically to the desired concentration and the reaction is maintained under a blanket of nitrogen. This methodology leads to a mixture of cross-linked and modified hemoglobins. Typically a very small amount (less than 5%) of unreacted hemoglobin is found in the resulting mixture. The cross-linked hemoglobins can be separated on large scale from uncross-linked ones using gel filtration under dissociating conditions. Ultrafiltration can be also be used to separate tetramers from dimers.

In a particularly preferred method of the invention using reagents such as benzene 1,3,5-tricarboxylic acid tris (methyl phosphate), fumaryl bis (methyl phosphate) and isophthaloyl bis (methyl phosphate) the reagent is slowly infused over a period of one hour to a final ratio of 2 mole of reagent to 1 mole of carbonmonoxy- or deoxy- hemoglobin at 60° C. Another hour at 60° C. after the completion of the infusion may increase the final yield in the case of modifying carbonmonoxyhemoglobin.

The modified hemoglobins of the invention may be intermolecularly linked to form polymerized hemoglobin. Polymerization may be accomplished by using glutaraldehyde, dialdehydes or polyaldehydes (Bonsen et al, U.S. Pat. No. 4,001,200)

The modified hemoglobins of the invention may be pasteurized using known methods (See for example Estep et al, In *Blood Substitutes*, Chang and Geyer (eds) Marcel Dekker, N.Y., (1989) and Estep U.S. Pat. No. 2,831,012). Pasteurization may be carried out at any stage of the process in the preparation of the modified hemoglobins of the invention using the above described preferred reagents as a result of the stability of the reagents and the specificity of the reagents for the DPG cleft of the hemoglobin.

The modified hemoglobin as in the present invention may be used as a blood substitute, red cell substitute, oxygen transfer agent and carrier, or plasma expander. The modified hemoglobin may be combined with a pharmaceutically acceptable carrier to prepare a pharmaceutical composition. Suitable pharmaceutically acceptable carriers include physiological saline, Ringer's solution, lactated Ringer's solution, Locke-Ringer's solution, Krebs-Ringer's solution, Hartmann's balanced saline and heparinized sodium-citrate-citric acid-dextrose solution. The modified hemoglobin may also be combined with other plasma substitutes and plasma expanders. Examples of plasma substitutes are poly(ethyleneoxide), polyvinylpyrolidone, polyvinyl alcohol and ethylene oxide-polypropylene glycol condensates and examples of plasma expanders are linear polysaccharides, including dextrans, albumin, other plasma proteins, pectins, balanced fluid gelatin and hydroxyethyl starch. The modified hemoglobin and pharmaceutical compositions containing the modified hemoglobin may be administered using conventional methods.

The modified hemoglobins of the invention are crosslinked in the DPG cleft and accordingly there are other free amino acid residues available for binding with other materials. Thus, the modified hemoglobins of the invention may also be bound to materials such as anticancer agents, antihypoxia agents and drugs.

The following general methods are used for the preparation, isolation and characterization of the modified hemoglobins of the present invention. (Reference may be made to Kavanaugh et al, Biochemistry 1988, 27, 1804–1808, which is incorporated herein by reference for a description of some techniques for the isolation and characterization of the modified hemoglobins).

A. Preparation of Hemoglobin

Any method that produces stroma free hemoglobin can be used to prepare the starting material for the preparation of the modified hemoglobins of the invention. It will also be appreciated that if the cross-linking reagents particularly described herein are used to prepare the modified hemoglobins of the invention it may not be necessary to use stroma free hemoglobin due to the specificity of the reagents.

The following method is selected because it gives high purity material to be used for cross-linking. Fresh, heparinized human blood is centrifuged at 600×X g for 20 min. Plasma and leukocytes are removed by aspiration and erythrocytes are resuspended in 2-3 volumes of 0.9% NaCl at 0° C. This procedure is repeated three times. Cells are then lysed by the addition of ice cold water 1:1 v/v, thoroughly mixed and allowed to stand on ice for 10 min. The hemolysate is thoroughly mixed with 2-3 mL of toluene to form an emulsion and then centrifuged at 27,000×X g at 0° C. for 40 min. The supernatant is carefully removed with a syringe from between erythrocyte stroma and toluene. The supernatant is then dialysed overnight against 4L of water containing 58 mg of $Na_2HPO_4$ (the membrane tubing is filled with carbon monoxide). After dialysis, the hemolysate is once again centrifuged at 27,000×X g for 60 min. at 4° C. and the pellet discarded. The hemoglobin is deionized by passage over a mixed bed resin ion exchange column equilibrated with double-distilled water. The top resin is AG 11A8, the middle AG 501X8 and the bottom AG 50WX4 taken in volume ratio 4:4:1 respectively. Hemoglobin solutions are stored under carbon monoxide at 4° C.

Preparation of deoxyhemoglobin is accomplished by photoirradiation of carbonmonoxyhemoglobin under a stream of humidified oxygen for 1 hour and then flushing with humidified nitrogen for two hours.

B. Molecular Mechanics Calculations

The molecular mechanics calculations were performed in accordance with the procedure set out in Kluger et al, J. Org. Chem. 1990, 55, 2864–2868, which is incorporated herein by reference. In particular, molecular mechanics calculations were performed on a microcomputer (Intel 80386 with 80387 coprocessor) using the program ALCHEMY II from Tripos Associates, St. Louis, Mo. The program uses standard force fields (described in the Tripos manual) for bond bending, bond stretching, out-of-plane distortions (for coplanar functional groups), torsional energies, and van der Waals repulsions. Minimization is iterative. The starting conformation for the calculation had the material fully extended.

C. Preparation of Reagents

The cross-linking reagents were prepared in two steps starting from di- or tricarboxylic acid di- or trichloride. Acyl bis and tris(dimethyl phosphates) are prepared in the reaction of acid chloride and sodium dimethyl phosphate in tetrahydrofuran. Acyl bis and tris(sodium methyl phosphates) were prepared in the reaction of acyl bis or tris(dimethyl phosphates) and sodium iodide in dry acetone. (See copending U.S. patent application Ser. No. 493,524, which is incorporated herein by reference, for details of the methods for producing the acyl phosphate esters). Other reagents which will give similar products in the cross-linking reaction are other derivatives of di- and tricarboxylic acids containing negative charges at each end. Thus, the tris (3,5-dibromosalicylate) ester of 1,3,5-benzene tricarboxylic acid, prepared from the reaction of 1,3,5-benzene tricarboxylic acid chloride with three equivalents of 3,5-dibromosalicylic acid and three equivalents of a tertiary amine in benzene, should produce a similar product on reaction with deoxyhemoglobin.

D. Selection of Reagents

A new class of cross-linking compounds, acyl bis(sodium methyl phosphates) have been described in U.S. patent application Ser. No. 493,524, which is incorporated herein by reference. Trifunctional cross-linkers for example, acyl tris(sodium methyl phosphates) are particularly useful in the present invention. The introduction of the third reactive functional group not only statistically increases the probability of the reaction with amino groups of hemoglobin but also increases the affinity of the highly anionic reagent to the DPG binding site. All three acyl phosphate groups can react with hemoglobin producing triply cross-linked species. If two of the three groups react to produce a linkage between the epsilon group lysine-82 of one chain and the alpha amino group of valine-1 of the other chain, the resulting product is also useful.

The preferred cross-linking reagent is 1,3,5-tricarboxylic acid tris(sodium methyl phosphate). It effectively cross-links hemoglobin producing a mixture of cross-linked hemoglobins in 60-75% yield under the conditions described below. The components of the mixture are shown in Table II.

E. The Cross-Linking Procedure.

Deoxyhemoglobin free of 2,3-diphosphoglycerate is used to produce derivatives cross-linked between beta chains. The reaction with the cross-linking agent and the hemoglobin can occur at a temperature of from 20° C. to 60° C. The pH of the reaction can vary from 6 to 8. The reaction can be carried out in an aqueous solution of buffers, including Bis-Tris-HCl, Tris-HCl, and HEPES. The concentration of buffer is typically 0.1M. The ratio of the cross-linking reagent to hemoglobin can vary from 2:1 to 10:1. The time of the reaction is up to 3 days at room temperature, or 3 hours at 60° C., for a sufficient degree of cross-linking to occur. The cross-linking reagent is introduced into the reaction vessel anaerobically to the desired concentration and the reaction is maintained under a blanket of nitrogen. This methodology leads to a mixture of cross-linked and modified hemoglobins. Typically a very small amount (less than 5%) of unreacted hemoglobin is found in the resulting mixture when the preferred cross-linking reagents are used to prepare the modified hemoglobins of the invention. The cross-linked hemoglobins can be separated on a large scale from uncross-linked ones using gel filtration under dissociating conditions. Ultrafiltration can also be considered as a means of separating tetramers from dimers.

F. Isolation and Analysis of Products Preparative Isolation of Hemoglobin by Liquid Chromatography The isolation and purification of single hemoglobin components is done by standard ion-exchange chromatography using DEAE-Sephacel and CM-Sephadex. Dilute hemoglobin solutions are concentrated by ultrafiltration, stored in the carbonmonoxy form on ice to minimize methemoglobin formation and denaturation.

Analytical and Preparative Separations of Hemoglobins by Ion Exchange HPLC Procedures Hemoglobins are separated by three different ion exchange HPLC procedures. For analytical purposes a 20×0.46 cm column of 5 microparticulate poly(aspartic acid) silica packing (PolyCAT A, Custom LC of Houston, Tex.,) is used according to the procedure of Ou et al (Ou et al., J. Chromatogr. 226, 197 (1983)). Another cation system in use for both analytical and preparative separations of hemoglobins uses a SynChropak CM300 column (250×4.1 mm for analytical and ×10 mm for preparative from SynChrom, Inc., Linden, Ind.) using developers containing 15 mM Tris-acetate at pH 8.0 and various gradients of sodium acetate starting at 10 mM and ending at 150 mM after procedures described by Huisman, J. Chromatog. 418:277, (1987). Separation of hemoglobins by anion exchange HPLC is done with SynChropak AX300 column (250×4.1 mm for analytical and ×10 mm for preparative) using developers 30 mM Bis-Tris pH 6.4 and various gradients of sodium acetate starting at 30 mM and ending at 300 mM. The effluent is monitored at 420 nm. Dilute hemoglobin solutions are concentrated by ultrafiltration.

Analytical and Preparative Separation of Globin Chains by Reversed Phase HPLC Heme and the globin chains are separated by reversed phase HPLC using 330 angstroms pore size C-4 Vydac columns (250×4.6 mm for analytical and 250×12 for preparative, The Separations group, Hesperia, Calif.) and developers containing 0.1% TFA and various gradients of acetonitrile starting at 20% and ending at 60% modified after a procedure of Shelton et al (J. Liq. Chromatogr. 7, 1969, (1984)). The effluent is monitored at 220 nm and the globin chains are recovered from the effluent by lyophilization.

Chemical Modification and Enzyme Hydrolysis of Globin Chains

For some studies cysteinyl residues are either oxidized to cysteic acid with performic acid or aminoethylated. Globin chains either with or without cysteinyl residues modified are hydrolyzed with trypsin (Worthington) carried out at room temperature (25° C.) in 80 mM ammonium bicarbonate buffer at pH 8.5 for 18-24 hours with a ratio of trypsin to globin of 1:50 by weight. In some cases the tryptic hydrolysis is followed by heating in boiling water for two minutes followed by hydrolysis with endoproteinase Glu-C from staphylococcus aeries V8 (Boehringer Mannheim Biochemical) at room temperature at pH 8.5 for 12-24 hours. During the course of these studies it has been found that more complete hydrolysis of some of the more resistant globin chain preparations can be obtained if the hydrolysis is carried out in the presence of either urea or sodium dodecyl sulfate (SDS). This was done by dissolving the globin in 8M urea and allowing it to stand at room temperature for two to four hours. This is then diluted to 2M urea with 80 mM ammonium carbonate buffer at pH 8.5 and hydrolyzed with trypsin (2% by weight) for 18-20 hours at room temperature. The tryptic hydrolysate is then heated in boiling water for two minutes, diluted to 1M urea with 80 mM ammonium carbonate buffer and hydrolyzed with endoproteinase Glu-C (1% by weight) for another 18-24 hours at room temperature. The hydrolysates are centrifuged or filtered through a 45 μm filter before injection onto an HPLC column.

Separation of Peptides by Reversed Phase HPLC

Peptide fragments are separated for both analytical and preparative purposes by HPLC procedures modified after that of Shelton et al. (Hemoglobin 9, 325 (1985)) using reversed phase C18 columns (25×0.46 cm Vydac, The Separations Group, Hesperia, Calif.). In some cases rechromatography is done with an ODS Ultrasphere C18 column (25×0.45 cm Altex/Beckman Instruments Berkeley, Calif.). Most separations are made using developers of 0.1% trifluoroacetic acid and gradients of acetonitrile starting at 0% and ending at 100% generated over a period up to 100 minutes. The typical gradient for both alpha and beta chain peptides starts at 0% acetonitrile and changes to 12.5% by 10 min., 25% by 60 min., 50% by 100 min. and 100% by 105 min. A second developer system adapted from the procedures of Schroeder et al (J. Chromatogr. 174, 385-392, 1979) and Wilson et al (J. Chromatogr. 179, 271-290, 1979) that uses 10 mM ammonium acetate buffer at pH 6.0 and acetonitrile concentration gradients was used in some cases for initial separation but more often for rechromatography. In all cases, the effluent is monitored at 214 nm which detects most peptides and also at either 280 nm to detect tyrosyl and tryptophanyl containing peptides or at 306 nm to detect peptides containing stilbene groups or 258 nm to detect the phthalylated peptides. Solvents and volatile solutes are removed from peptides in the effluent by lyophilization or vacuum evaporation.

Amino Acid Analysis

Peptides are hydrolyzed in evacuated tubes using 6M HCl vapor at 110° C. for 22 hours. In some cases a hydrolysis time of 48 or 72 hours is used if Val-Val or other resistant bonds are present. The amino acids are derivatized with phenyl isothiocyanate and the resultant phenylthiocarbamyl amino acid derivatives are separated by reversed phase HPLC using an IBM octadecyl silane column (IBM Instruments Inc.). Effluent is monitored at 254 nm and the signal is recorded and integrated with the IBM Systems 9000 computer.

Polyacrylamide Gel Electrophoresis

The extent of cross-linking of globin chains is determined by polyacrylamide gel electrophoresis in the presence of 0.1% sodium dodecyl sulfate (SDS-PAGE) according to the procedure of Laemmli (U.K., Nature (London) 227, 680 (1974)). A 15% polyacrylamide gel that is 2.7% cross-linked is used. The hemoglobins and globins from HPLC separation are prepared by heat denaturation in a buffer containing 65 mM Tris-HCl pH 6.8, 2% SDS, 10% v/v glycerol, and 5% v/v 2-mercaptoethanol. Approximately 5-20 μg of protein is applied to the gel and electrophoresed at 20 mA for about 8 hours. The extent of cross-linked hemoglobins is determined by passing a sample through a column of Sephadex 100 superfine under dissociating conditions (1M $MgCl_2$).

Electrospray Mass Spectrometry

Electrospray mass spectrometry of modified globin chains was carried out using a Sciex Atmospheric Pressure Ionization Mass Spectrometer (Thornhill, Canada) and the method described by Fenn, J. B. et al. in Science, 246, 64-70, 1989.

Measurement of Functional Properties of Isolated Hemoglobins

The hemoglobin-oxygen equilibrium properties of modified hemoglobins are measured with the automatic recording method of Imai (Imai, K., Methods Enzymol. 76, 438 (1981)). The data are analyzed according to the Adair stepwise oxygenation scheme described by Imai (Imai, K., Methods Enzymol. 76, 438 (1981)) using apparatus and on-line laboratory computer described by Shih and Jones (Shih, D. T., and Jones, R. T., Methods Hematol. 15, 125 (1986)). The conditions are 50 μM Bis-Tris, pH 7.4, 0.1M $Cl^-$, 25° C., and 55 μM heme. Parameters measured are the oxygen pressure for half saturation ($P_{50}$) and Hill's coefficient of cooperativity at half saturation (n).

The following examples are further provided for illustrative purposes only and are in no way intended to limit the scope of the present invention.

EXAMPLE 1

Benzene 1,3,5-tricarboxylic acid tris(sodium methyl phosphate) was prepared from benzene 1,3,5-tricarboxylic acid tris(dimethyl phosphate), (prepared from sodium dimethyl phosphate and 1,3,5-benzene tricarbonyl trichloride) and sodium iodide as set forth in U.S. patent application Ser. No. 493,524, which is incorporated herein by reference. Isophthaloyl bis(methyl phosphate), fumaryl bis(methyl phosphate), and 3,3'-stilbene bis(methyl phosphate) were also prepared as taught in copending U.S. patent application Ser. No. 493,524.

Cis-1,3,5-cyclohexanetricarboxylic acid tris (sodium methyl phosphate) was prepared as follows. 50 ml thionyl chloride was added to 8.6 g (0.04 mol.) cis-1,3,5-cyclohexanetricarboxylic acid, then 1 ml of dimethyl formamide was added and the mixture heated to 40° C. until evaporation of gas ceased and the solution became clear (approximately 2 hours). Excess thionyl chloride was evaporated in a rotary evaporator. The resulting product, cis-1,3,5-cyclohexanetricarbonyl trichloride (1.1 g, 4 mmol) was reacted with sodium dimethyl phosphate (1.78 g, 12 mmol) in 50 ml dry tetrahydrofuran, as set forth in U.S. patent application Ser, No. 493,524. The mixture was stirred under nitrogen at room temperature for four hours. The solution was then filtered and the solvent evaporated giving 2.1 g of cis-1,3,5-cyclohexanetricarboxylic acid tris (dimethyl phosphate) in a yield of 96%. The structure was confirmed by proton nmr as described in Kluger et al, J. Org. Chem. 55:286 (1990). 2.4 g (4.4 mmol) cis-1,3,5-cyclohexanetricarboxylic acid tris (dimethyl phosphate) in 40 ml dry acetone was combined with 2.0g sodium iodide in 40 ml acetone. The product precipitated as a yellow powder. The reaction mixture was left overnight, filtered under nitrogen, washed with acetone and dried under vacuum. The product, cis-1,3,5-cyclohexane-tricarboxylic acid was obtained in 90% yield and the structure confirmed by proton and phosphorus nmr, as described in Kluger et al, J. Org. Chem. 55:286 (1990). 5 g cis-1,3,5-cyclohexane-tricarboxylic acid was refluxed with 20 ml of acetic anhydride and 1.0 g sodium acetate for 4 hours. The base was removed by refluxing for 2 hours with 10 ml of acetyl chloride. Excess acetyl chloride was removed by distillation at a temperature of 132° C. The residual liquid mixture containing some sodium chloride crystals was poured into 400 ml water. Evaporation to 5 ml and cooling gave a crystal crop, which was recrystallized from water.

1,3,5-trans-cyclohexanetricarboxylic acid was synthesized by epimerization of commercially available cis isomer following the method of Steitz (J. Org. Chem. 33:2979, (1968)). Trans-1,3,5-cyclohexanetricarboxylic acid tris (dimethyl phosphate) and trans-1,3,5-cyclohexanetricarboxylic acid tris (sodium methyl phosphate) were obtained by the same reactions as the cis isomers from the trans acid.

Carbon monoxide was removed from carbonmonoxyhemoglobin, by photoirradiation under a stream of humidified oxygen for 60 min. at 0° C., following the general methods of Kavanaugh et al. (Biochem. 27:1804 (1988)). The protein was subsequently deoxygenated in a modified rotary evaporator apparatus by passing a stream of humidified nitrogen for 3 hours at 35° C. through the sample.

Chemical modification of deoxyhemoglobin with benzene 1,3,5-tricarboxylic acid tris (sodium methyl phosphate) was carried out as follows. 5 ml of deoxyhemglobin and 0.5 ml of 1M bis-tris-HCl buffer at pH 7.2 in a rotary reaction apparatus under nitrogen was treated with 2-3 ml of the buffered solution of 1,3,5-benzentricarboxylic acid tris (sodium methyl phosphate) at 36° C. The quantity of the cross-linker and the buffer was such that the final concentrations after the injection of the solution of the cross-linker was 1 mM in hemoglobin and 0.1M in buffer and 3 mM in the cross-linker. The hemoglobin was allowed to react for 3 days. The product was converted to the carbonmonoxy form and analyzed by HPLC, tryptic digest, and amino acid analysis. Modification of deoxyhemoglobin with isophthaloyl bis(methyl phosphate), fumaryl bis(methyl phosphate), 3,3'-stilbene bis(methyl phosphate) and cyclohexyl 1,3,5 tricarboxyl tris sodium methyl phosphate was carried out using the above procedure. Product was isolated by ion exchange chromatography using DEAE-Sephacel and CM-Sephadex. For analysis, globin chains were separated on reverse phase HPLC.

In order to determine the extent of cross-linking a 0.1 mL sample of the reaction mixture was passed through a column of Sephadex 100 superfine using 1.0M $MgCl_2$ as an eluent.

The structure of modified globins of major components resulting from reaction with the fumaryl, isophthaloyl, 3,3'stilbenedicarbonyl, 1,3,5-tricarboxylic and cyclohexane compounds are summarised in Table II.

Table I summarizes the distances between $\beta 1Val-NH_2$ and $\beta 82-lys-NH_2$ in oxy- and deoxyhemoglobin and the linkage distance of some of the compounds of the present invention. The data in Table I shows that the length of the cross-linking reagents is not identical to the distances between the $\beta$ chains, at the linkage sites of the unmodified hemoglobins. For example, isophthaloyl bis (methyl phosphate) has a linkage distance of 7.3 angstroms and cross-links deoxyhemoglobin between $\beta 1$ and $82\beta$. In unmodified deoxyhemoglobin the distance between $\beta 1$ and $82\beta$ is 11.5 angstroms.

Representative detailed results for hemoglobins modified with 1,3,5-benzenetricarboxylic acid tris(sodium methyl phosphate), isophthaloyl bis(methyl phosphate), and cyclohexyl 1,3,5 tricarboxyl tris sodium methyl phosphate are discussed below.

A. Deoxyhemoglobin modified with 1,3,5-benzene tricarboxyl tris (methyl phosphate)

Figure 2:
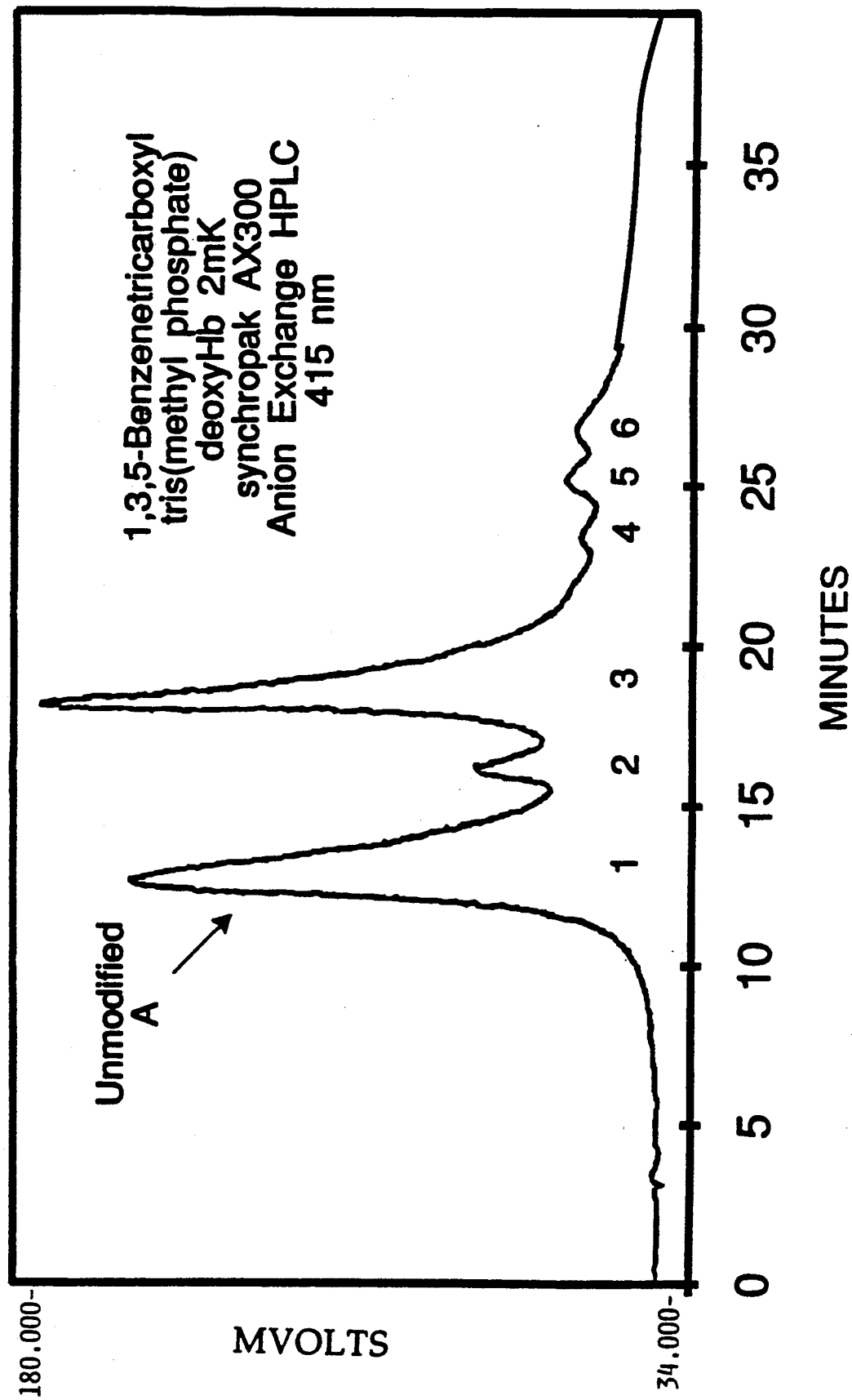
FIG. 2 shows an anion exchange HPLC chromatogram of the reaction products resulting from treatment of deoxyhemoglobin with 1,3,5-benzene tricarboxyl tris (methyl phosphate)
Figure 3:
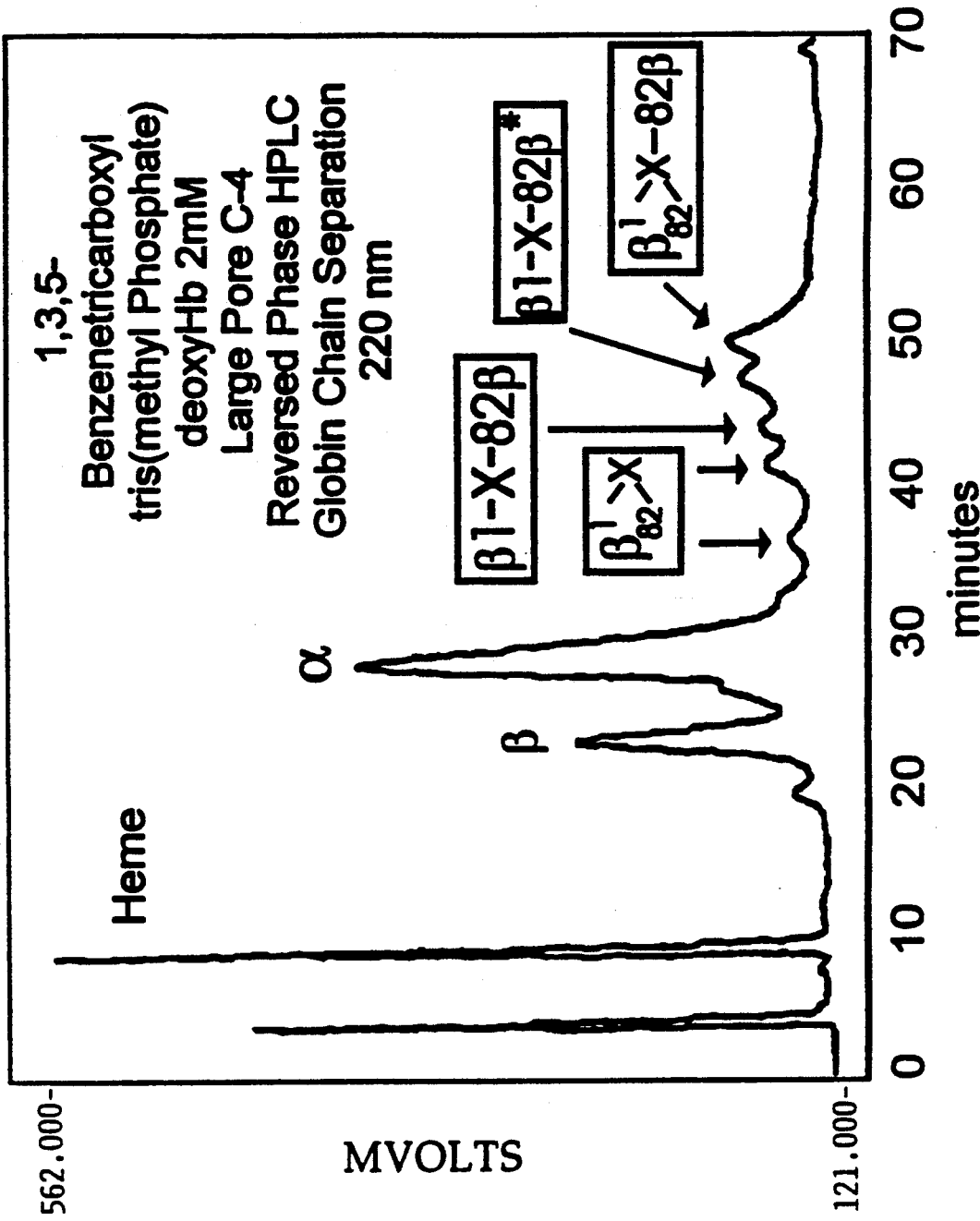
FIG. 3 shows the globin chain separation of the 1,3,5-benzene tricarboxyl tris(methyl phosphate) treated hemoglobin, identifying the globin zones.

The analysis of the products of deoxyhemoglobin modified with 1,3,5-benzene tricarboxyl tris (methyl phosphate) is shown in FIG. 2. The anion exchange HPLC chromatogram in FIG. 2 shows the separation of modified and unmodified products on a preparative size Synchropak AX 300 anion exchange column. The modified hemoglobins were further purified by rechromatography on a preparative size CM 300 cation exchange column. Zones from cation exchange rechromatography were then subjected to globin chain separation using Vydak C-4 large pore reversed phase columns. The results of globin chain separation are shown in FIG. 3. Eight zones can be distinguished.

The globin chains from each of zones 4 to 8 were isolated, treated by oxidations or aminoethylation to stabilize the cysteinyl residues, hydrolyzed with trypsin and glu-C proteinase and the resultant peptides were separated and analyzed for amino acid composition.

Figure 4:
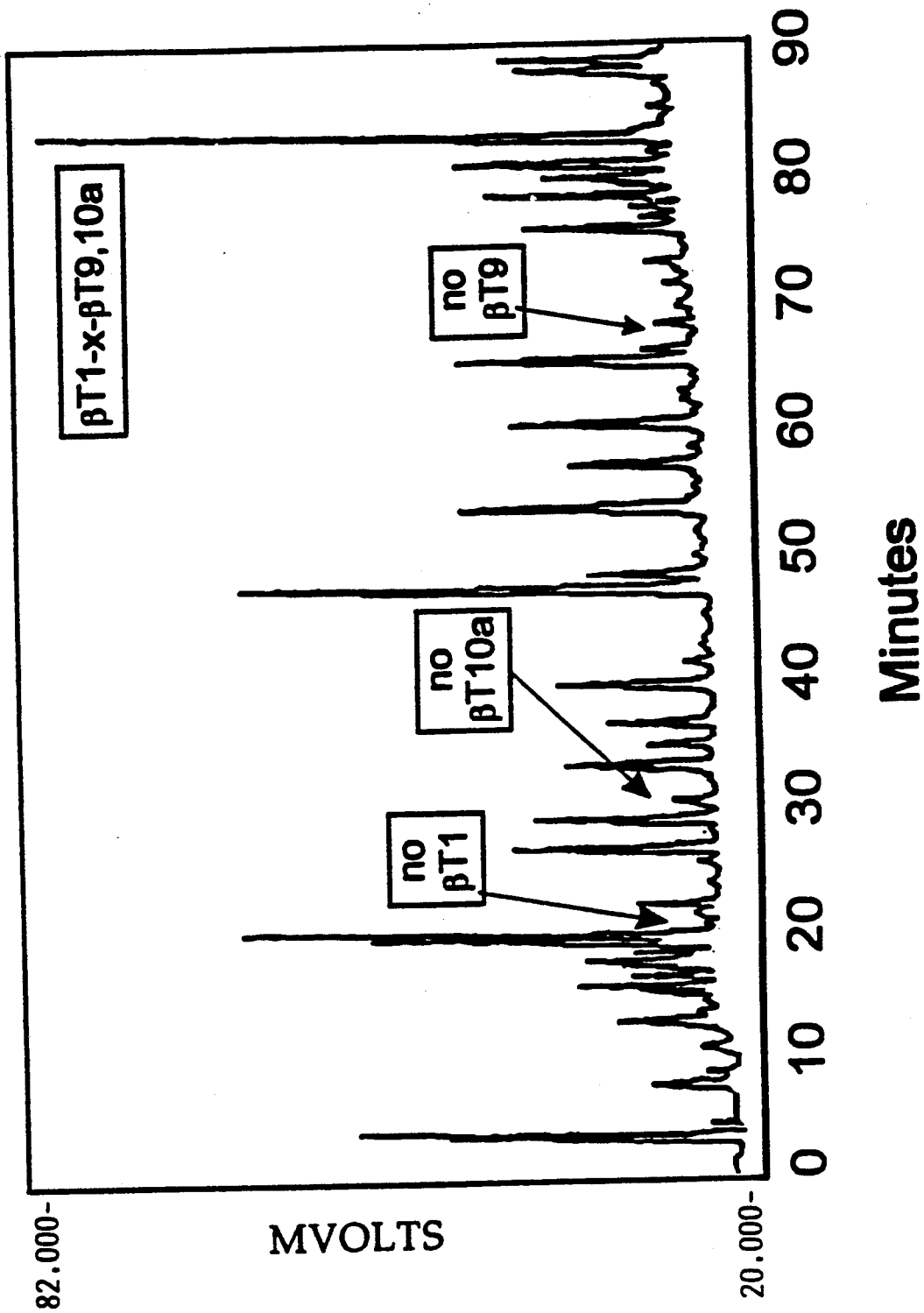
FIG. 4 shows the peptide pattern of zone 4 from FIG. 3.

FIG. 4 is an analytical profile of the peptides derived from zone 4 which establishes modification of the globin chains at $\beta^1_{82}>X$-. SDS gel electrophoresis confirmed that the globin was a single chain and not crosslinked.

Figure 5:
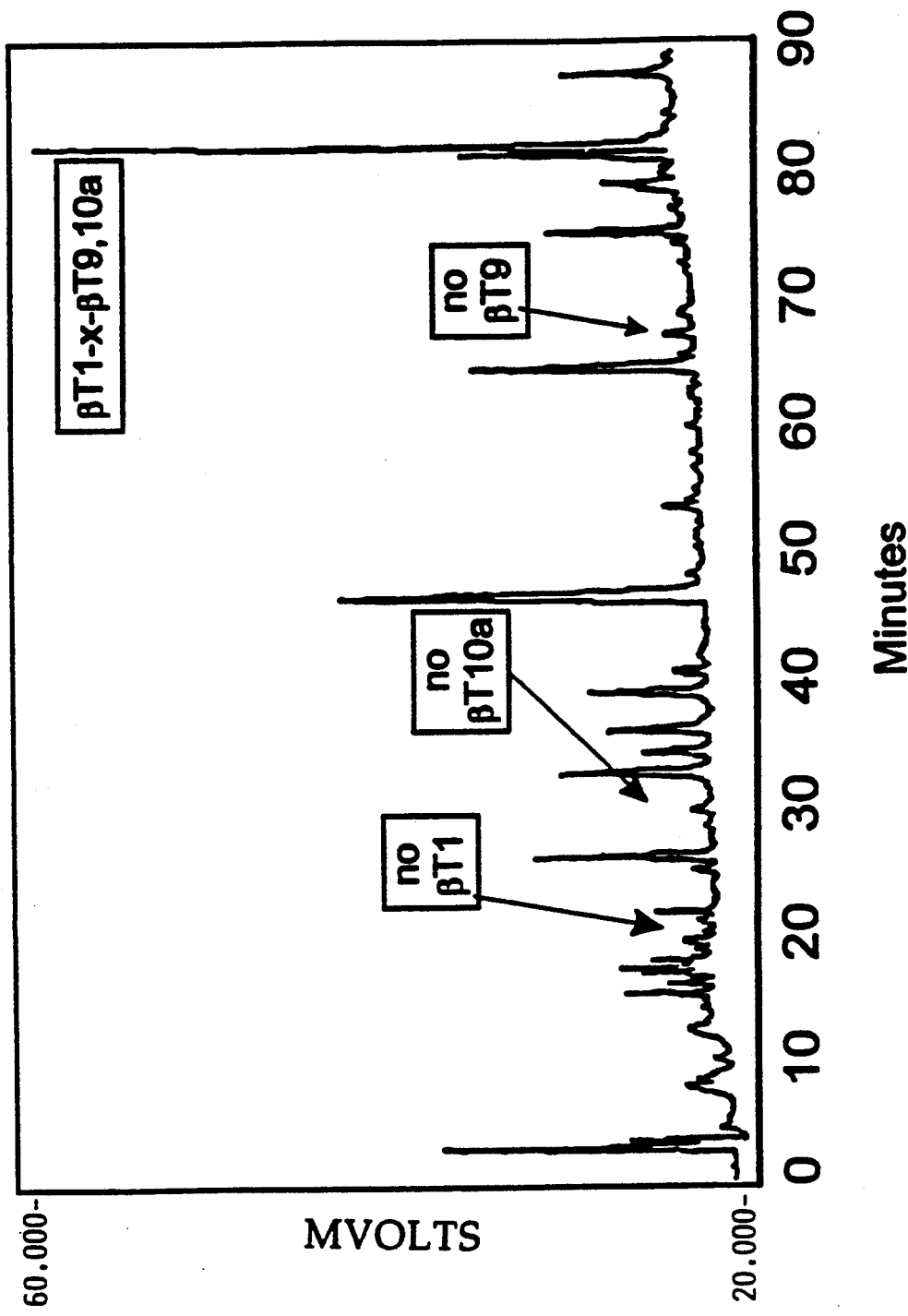
FIG. 5 shows the peptide pattern of zone 5 from FIG. 3.

FIG. 5 is an analytical profile of the peptides derived from zone 5 which establishes modification of the globin chain at $\beta^1_{82}>X$-. SDS gel electrophoresis indicates the presence of a single chain and not cross-linked chains. The results suggest that a methyl phosphate group is present on the X-linker to give the structure $\beta^1_{82}>X$-methyl phosphate.

Figure 6:
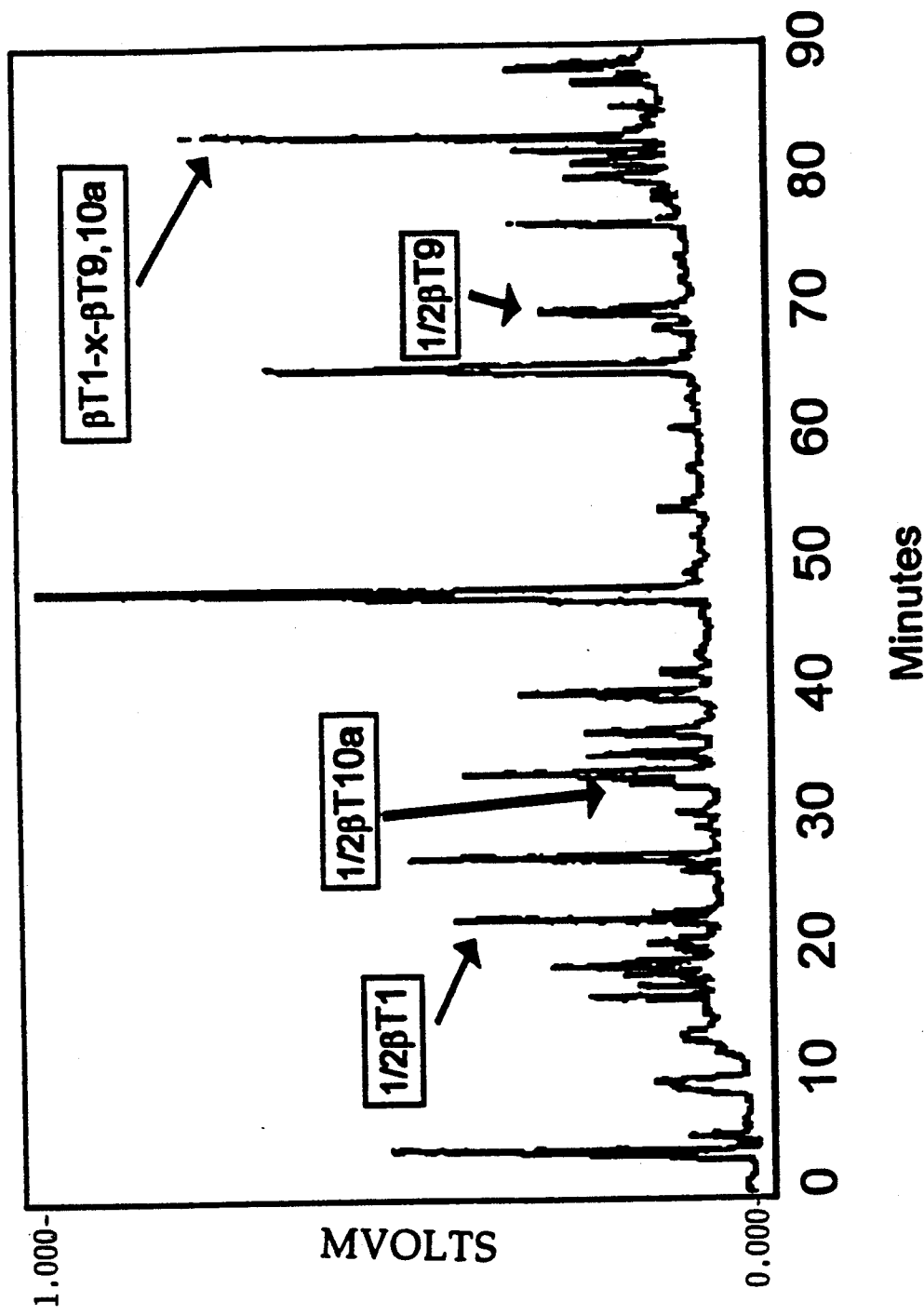
FIG. 6 shows the peptide pattern of zone 6 from FIG. 3.

FIG. 6 is an analytical profile of the peptides derived from zone 6 which establishes a modified globin of the structure $\beta 1$-X-$82\beta$. SDS gel electrophoresis confirmed the presence of two cross-linked beta chains.

Figure 7:
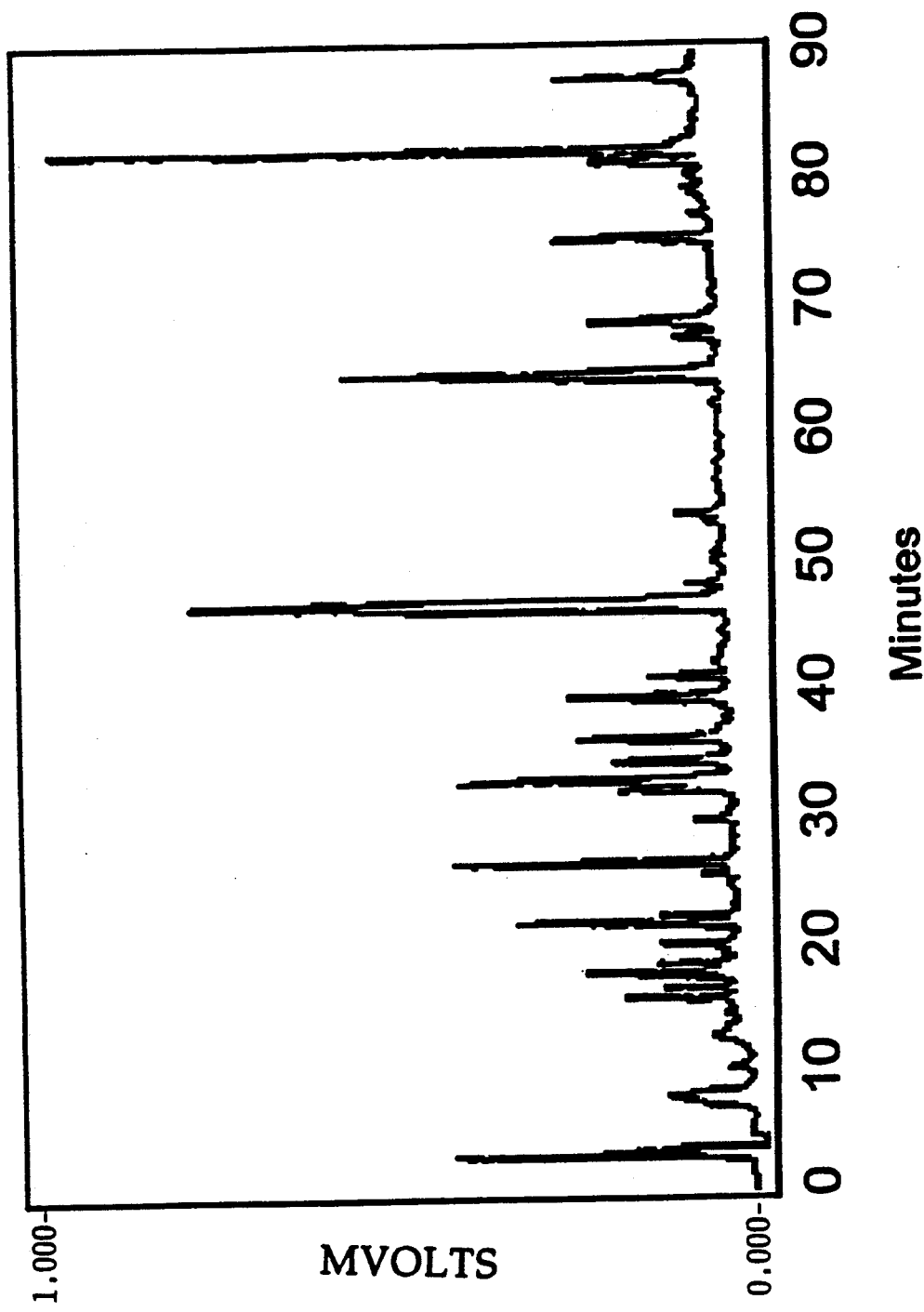
FIG. 7 shows the peptide pattern of zone 7 from FIG. 3.

FIG. 7 is an analytical profile of the peptides derived from zone 7 which establishes a modified globin of the structure $\beta 1$-X-$82\beta$. SDS gel electrophoresis confirmed the presence of two cross-linked beta chains. Preliminary results indicate that a methyl phosphate group is also present in the cross-linker as

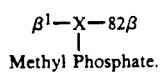

Methyl Phosphate.

Figure 8:
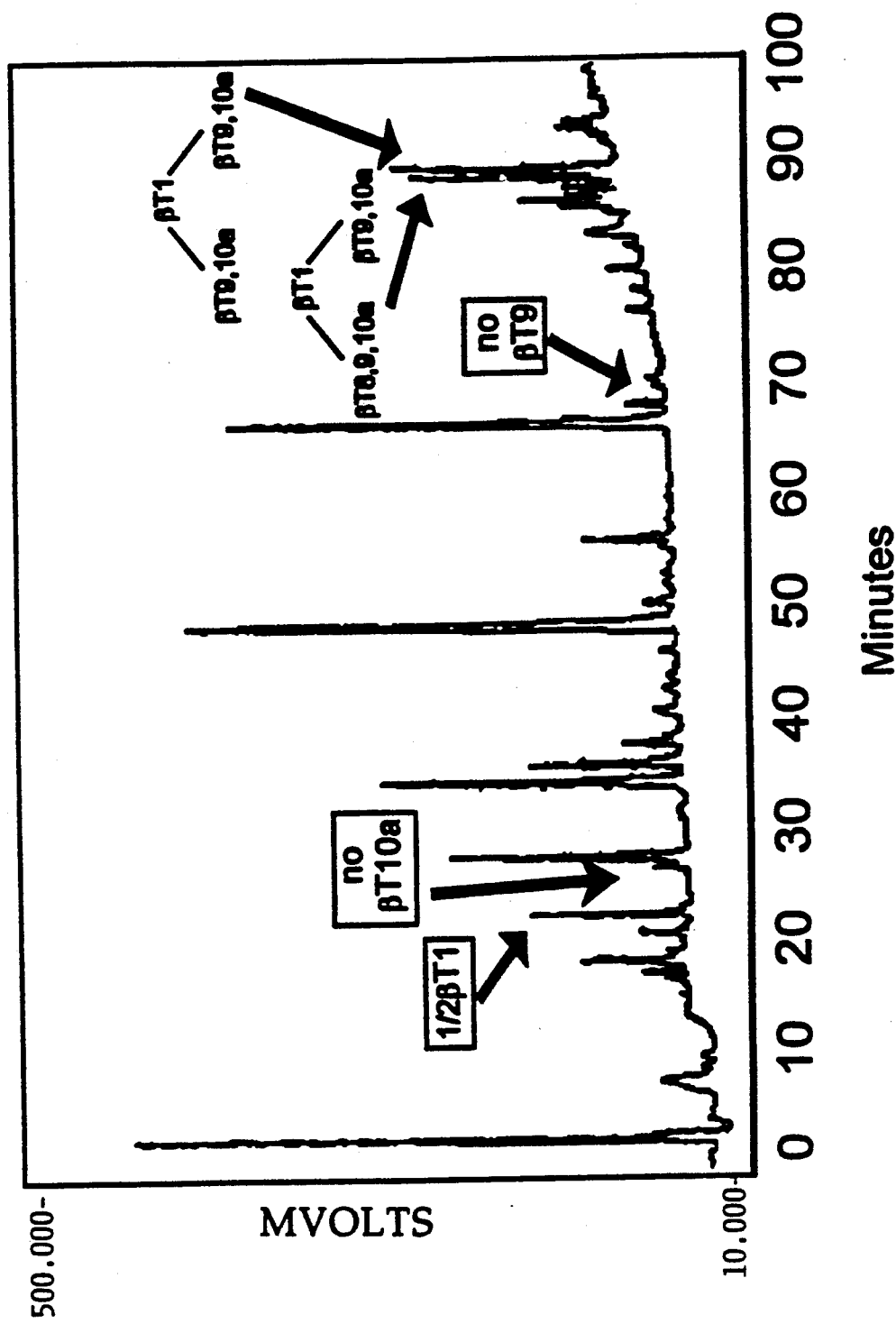
FIG. 8 shows the peptide pattern of modified globin corresponding to zone 8 from FIG. 3, illustrating the $\beta^1{}_{82} > X\text{-}82\beta$ cross-linked hemoglobin.
Figure 9:
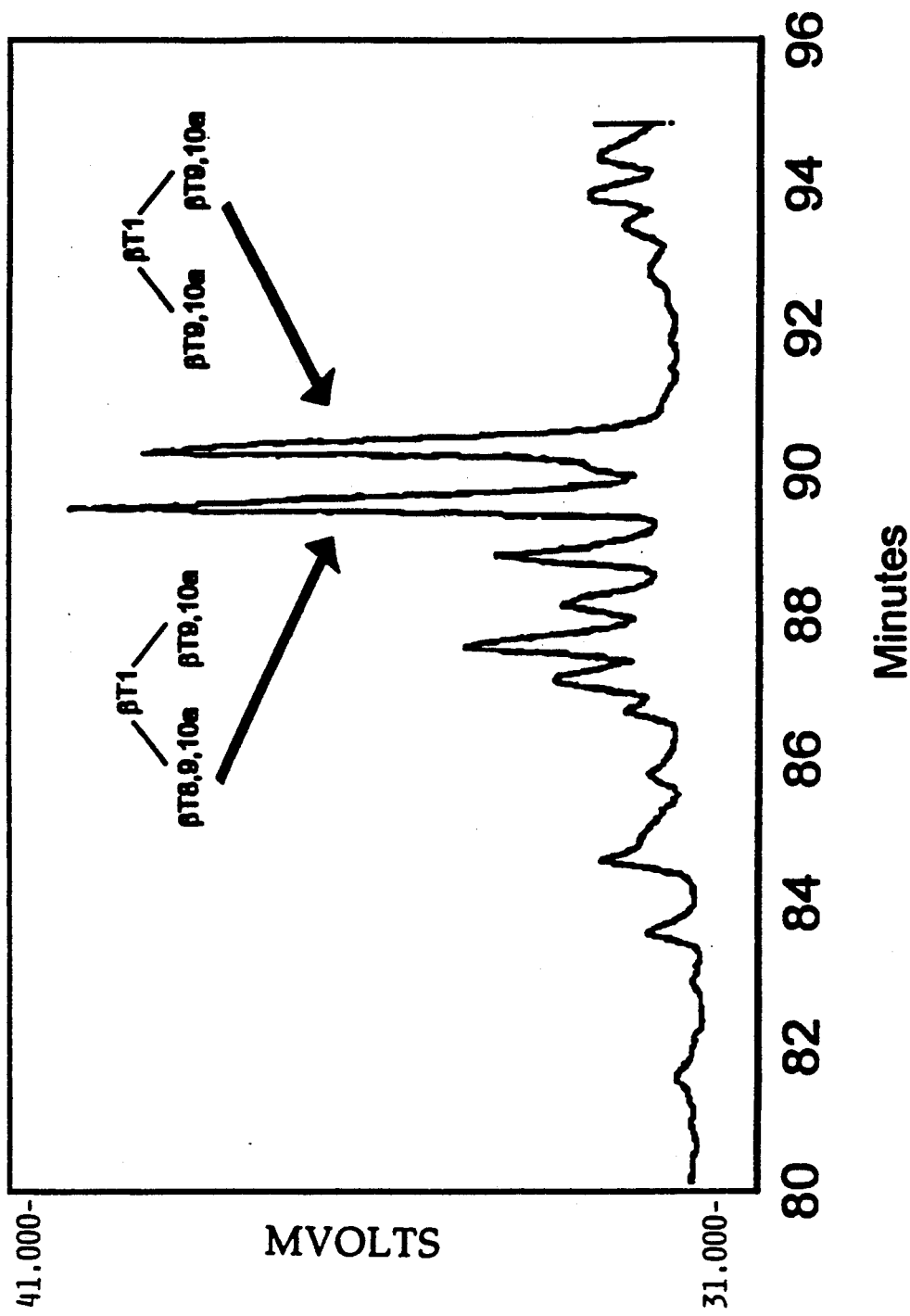
FIG. 9 shows an expansion of the end of the peptide pattern shown in FIG. 7 using a wavelength of 257 nm in the detector.
Figure 10:
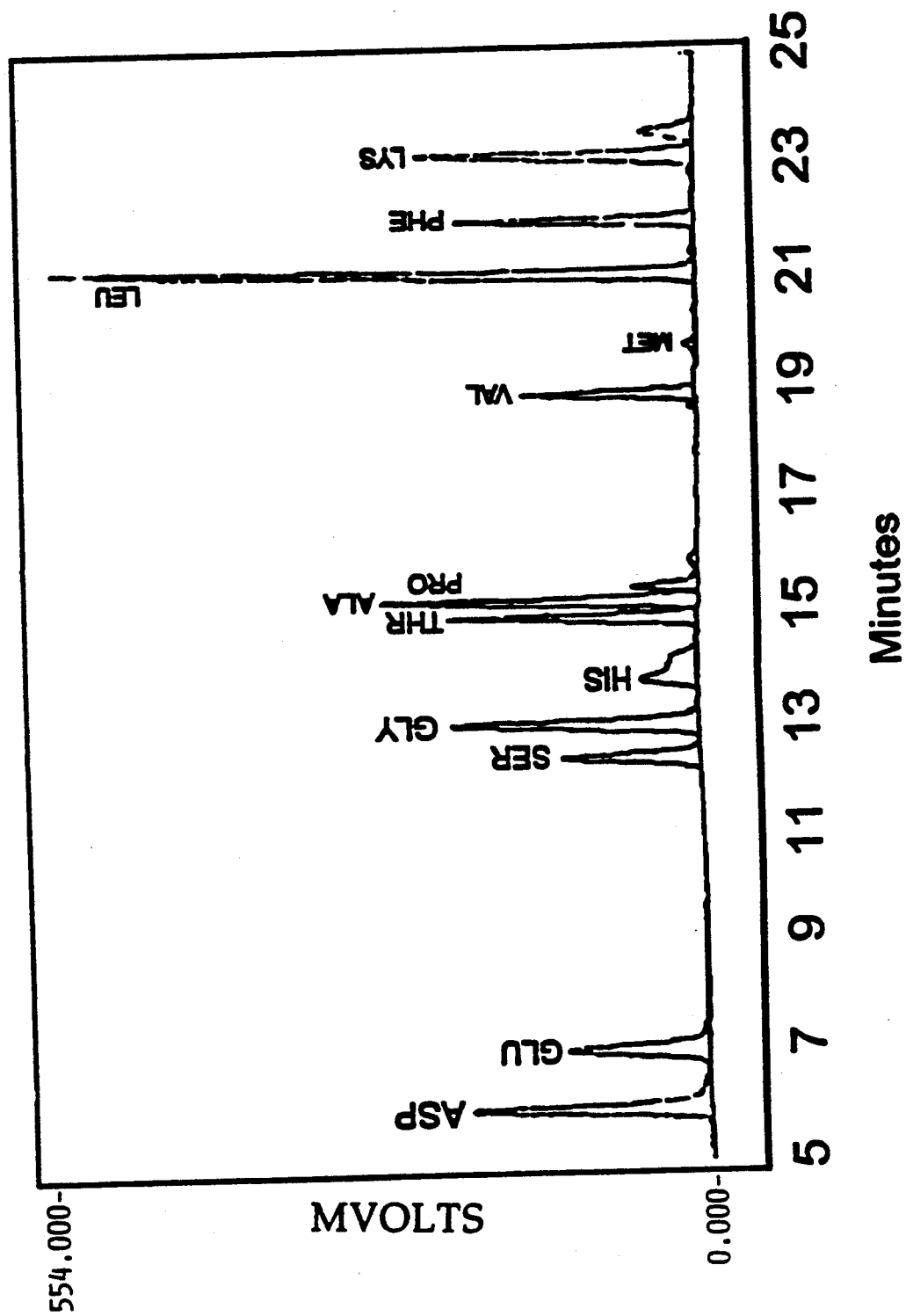
FIG. 10 shows the amino acid analysis of the modified peptide from the $\beta^1{}_{82} > X\text{-}82\beta$ cross-linked hemoglobin.

FIG. 8 is an analytical profile of the peptides derived from zone 8 which establishes a modified globin of the structure $\beta^1_{82}>T$-$82\beta$. Resolution of the end of this profile was expanded with a detector wavelength of 257 nm which is sensitive to the cross-linking and other aromatic compounds. The expanded profile is shown in FIG. 9. The two peptides shown differ by one lysyl residue due to incomplete hydrolysis of $\beta t8$. Amino acid analysis of the modified peptide is shown in FIG. 10 which confirms the site of the cross-link as $\beta^1_{82}>T$-$82\beta$.

Figure 11:
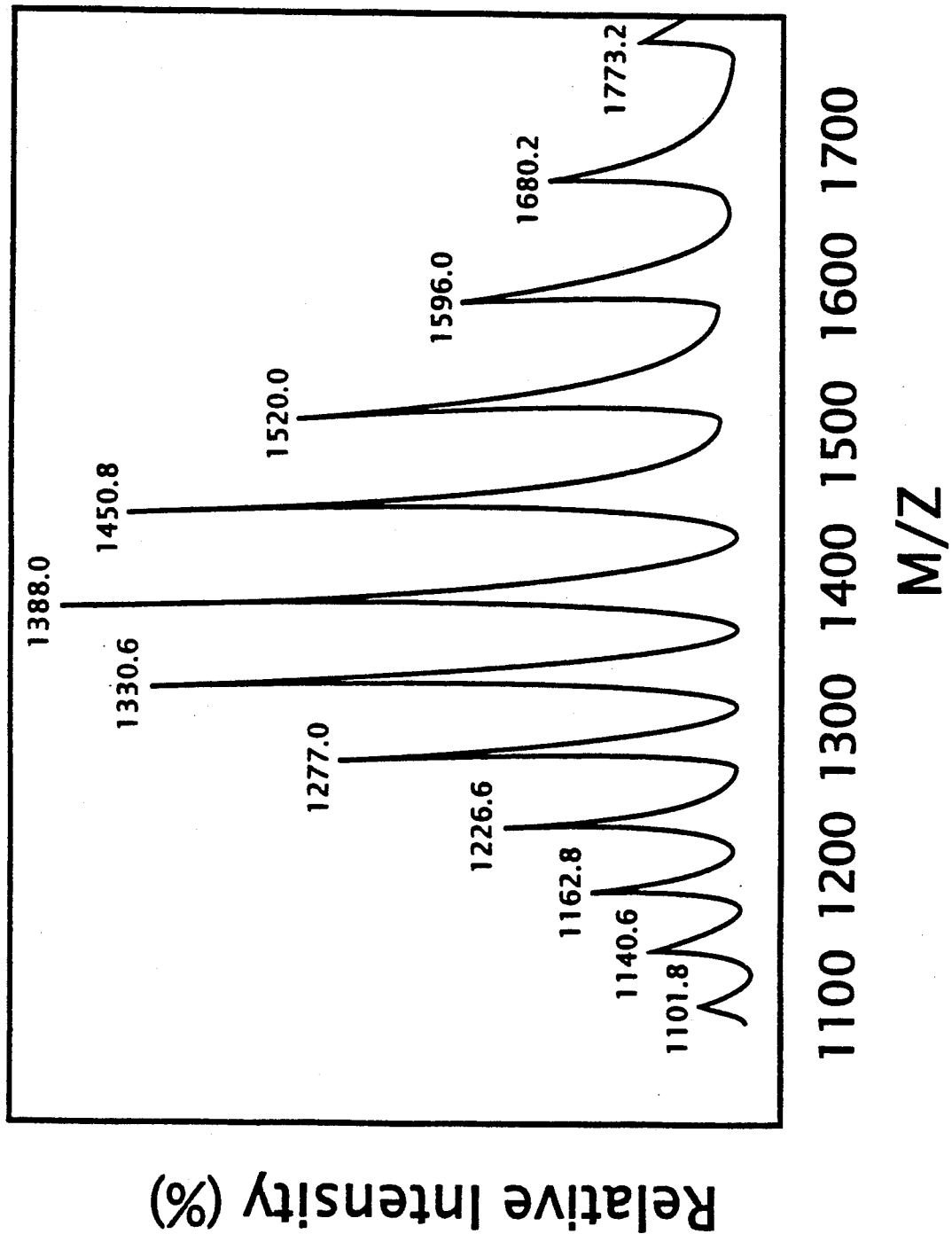
FIG. 11 shows an electrospray mass spectrum of $\beta^1{}_{82} > X\text{-}82\beta$ hemoglobin cross-linked with 1,3,5-benzene tricarboxylic acid tris (methyl phosphate) which has a molecular weight consistent with the stated structure.

Electrospray mass spectra of the modified hemoglobins was obtained using the methods described above. The electrospray mass spectra is shown in FIG. 11 and an analysis is presented in Table III. The data demonstrates that the observed molecular weight is consistent with the structure of two beta chains cross-linked with a benzene tricarboxyl bridge.

B. Deoxyhemoglobin modified with isophthaloyl bis (methyl phosphate)

Figure 12:
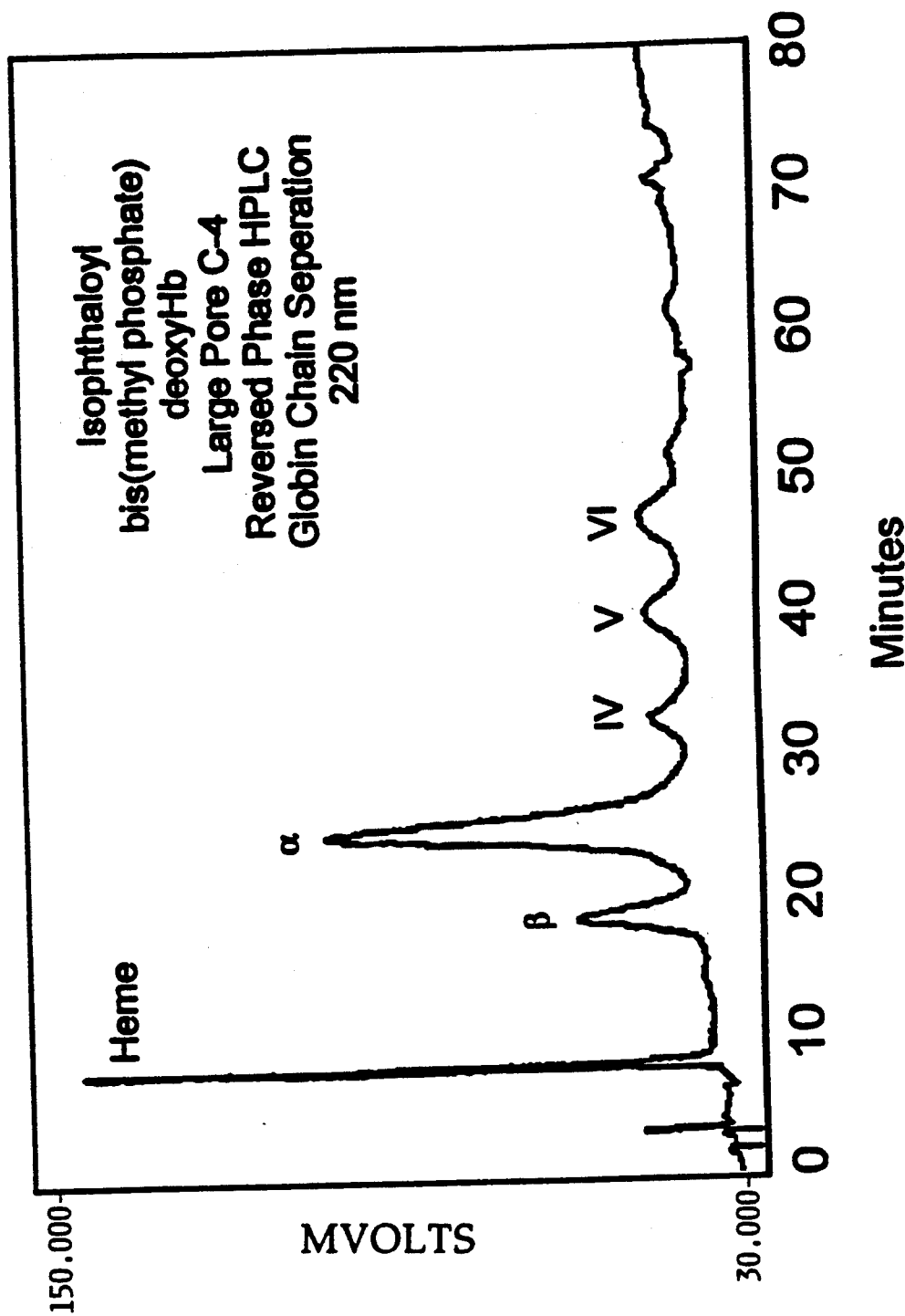
FIG. 12 shows the globin chain separation for isophthaloyl bis (methyl phosphate) modified deoxyhemoglobin.

The products of deoxyhemoglobin modified with isophthaloyl bis (methyl phosphate) were analyzed by anion exchange HPLC on preparative size Synchropak AX 300 anion exchange column. The modified hemoglobins were further purified by rechromatography on a preparative size CM 300 cation exchange column. Zones from cation exchange rechromatography were then subjected to globin chain separation using Vydak C-4 large pore reversed phase columns. The results of globin chain separation are shown in FIG. 12.

Figure 13A:
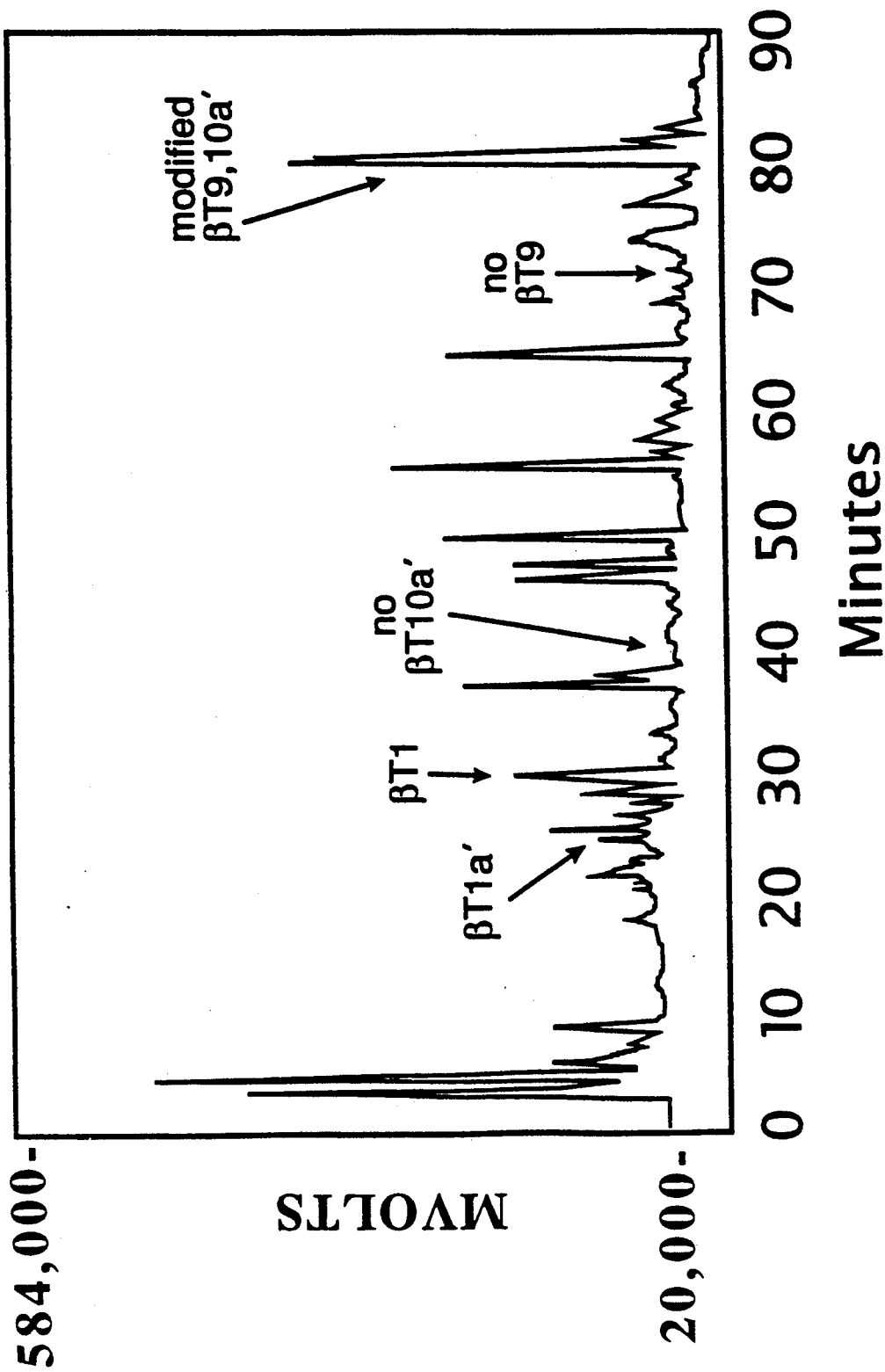
FIGS. 13 A, B and C show analytical profiles for deoxyhemoglobin modified with isophthaloyl bis (methyl phosphate) from zones IV(A), V(B) and VI(C) of FIG. 12.
Figure 13B:
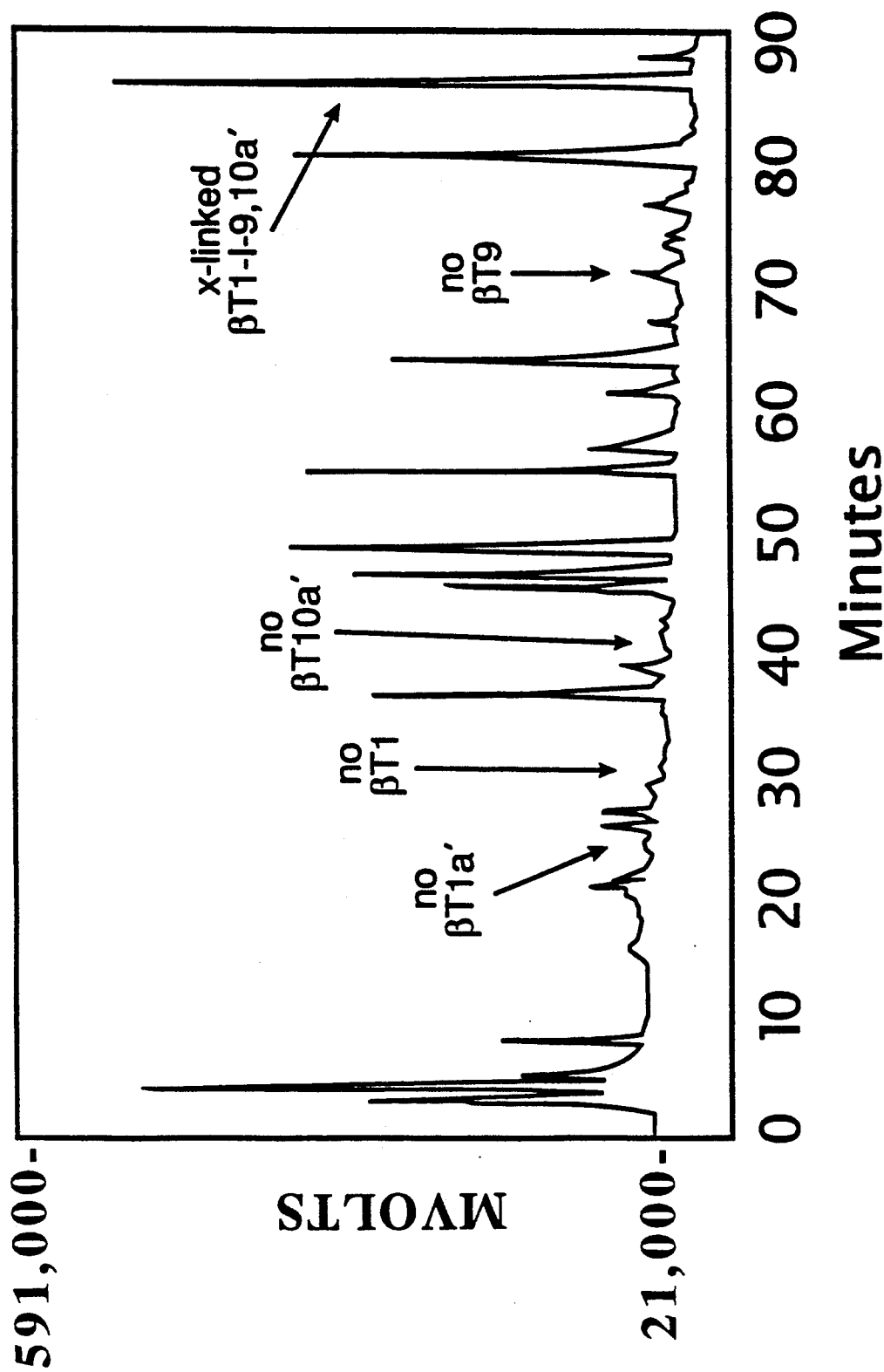
Figure 13C:
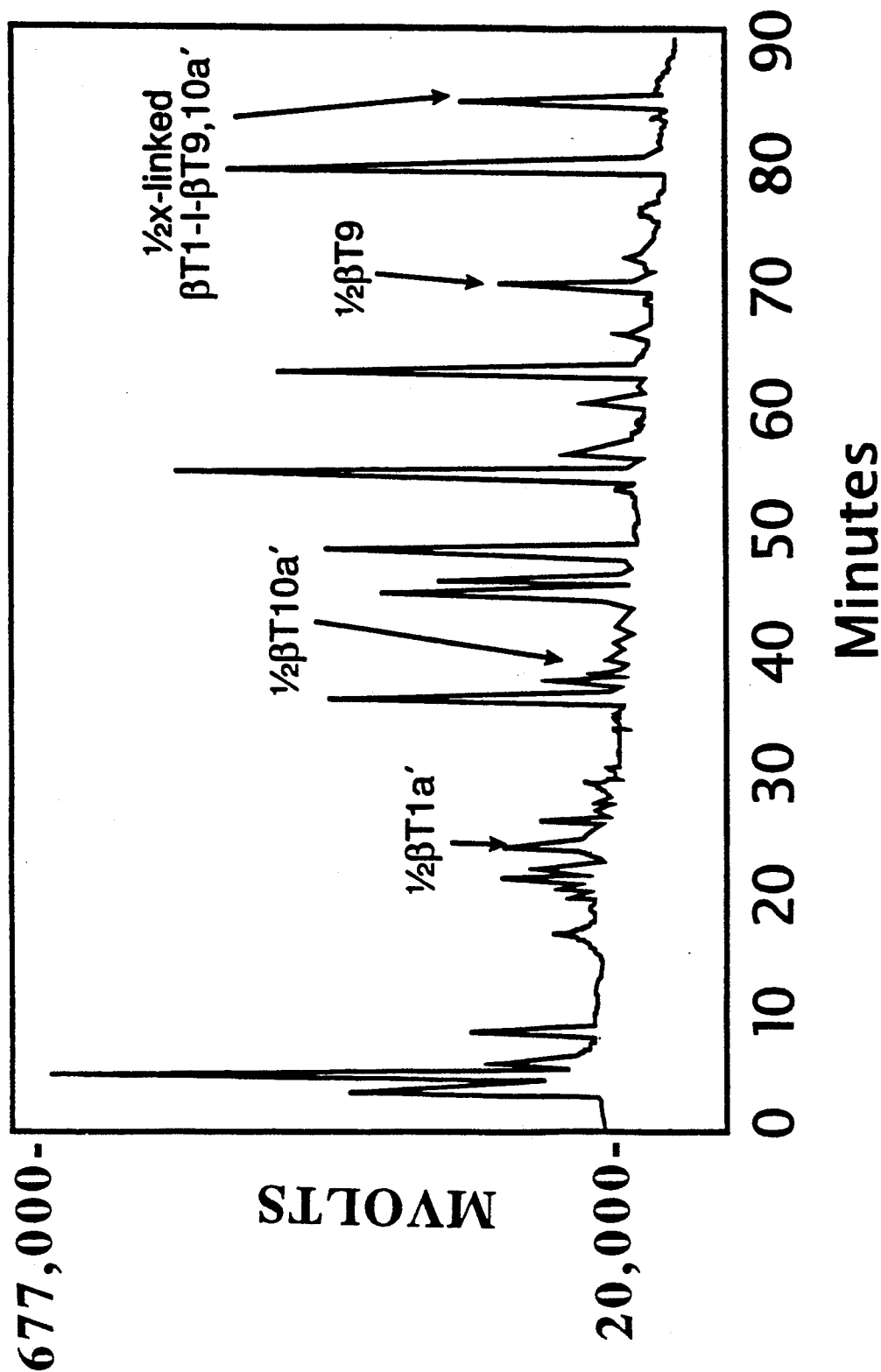

The globin chains from each of zones IV to VI were isolated, treated by oxidations or aminoethylation to stabilize the cysteinyl residues, hydrolyzed with trypsin and glu- C proteinase and the resultant peptides were analyzed. FIGS. 13 A, B and C show analytical profiles of the peptides derived from zones IV to VI which establishes the site of cross-linking for the derivatives between the epsilon amino group of lysine 82 of one beta chain to the alpha amino group of valine 1 of the other beta chain. Table IV summarizes the structures of the isophthaloyl modified hemoglobins from zones IV to VI.

C. Deoxyhemoglobin modified with cis or trans cyclohexyl 1,3,5 tricarboxylic tris (sodium methyl phosphate)

Deoxyhemoglobin was modified as follows. 5 ml of deoxyhemoglobin and 0.5 ml of 1M bis-tris-HCl buffer (pH 7.2) in a rotary reaction apparatus under nitrogen was treated with 2-3 ml of a buffered solution of cis-1,3,5-cyclohexanetricarboxylic acid tris (sodium methyl phosphate) at 60° C. The quantity of the cross-linker and the buffer was such that the final concentrations after the injection of the solution of the cross-linker was 1 mM in hemoglobin and 0.1 M in buffer. Three equivalents of the cross-linker were injected. The reagent was added by syringe pump (reagent at room temperature) during one hour and the reaction continued for two hours at 60° C. After reaction, the cooled product was converted to the carbonmonoxy form and analyzed by HPLC, tryptic digest, and amino acid analysis. There was approximately 75% cross-linked material produced and the primary species was triply cross-linked, from beta-1-lys-82 to beta-22--val-1 and beta-2-lys-82, with additional material singly cross-linked beta-1-lys-82 to beta-2-val-1. The material had a useful oxygen affinity and good cooperativity (as shown in Table II). The following structures have been tentatively identified from peptide analysis of the products: $\alpha_2\beta^1$-X-82$\beta$, $\alpha_2\beta^1{}_{82}$>X-82$\beta$, $\alpha_2\beta^1{}_{82}$>X-82$\beta$1-X, $\alpha_2(\beta 82$-X$)_2$, $\alpha_2(\beta 82$-X-MePO$_4)_2$, $\alpha_2(\beta 82$-X=2Me PO$_4)_2$.

EXAMPLE 2

Functional analysis of modified hemoglobins

The hemoglobin-oxygen equilibrium properties of the modified hemoglobins of Example 1 were measured in 50 mM bis tris, 0.1M Cl-, pH 7.4, 25° C., 55 μm Heme as described above and the results are shown in Table II. Note that normal, unmodified Hb A has a $P_{50}$ (oxygen tension necessary to half-saturate) of 4.9 (higher values are needed for a good red cell substitute) and a Hill coefficient of 2.9. Values over 2 are necessary for effectiveness. Listings are for carboxyl derivatives. $P_{50}$ is listed with Hill coefficient in parentheses. It is interesting to note that the two different components, each of which is cross-linked between $\beta$1Val of one chain and the $\beta$82Lys of the other chain, have decreased affinities for oxygen ($P_{50}$ to 17 mm Hg). One of these has its third carboxyl group linked internally to the $\beta$82Lys of the first chain whereas the other component has this carboxyl group free; however, a second benzene tricarboxylate is attached to this $\beta$82Lys. The affinity of the $\alpha_2\beta 82$-X 82$\beta$ hemoglobin cross-linked with the isophthaloyl bridge, is similar namely 17.0 to 17.8 mm Hg. It would appear that linking the $\beta$1Val to $\beta$82Lys of the other chain with a 1,3 dicarboxyl benzene bridge results in the same affinity regardless of what is present at the 5 position of the cross-linker and whether or not the other $\beta$82Lys group is free or modified. Similarly, the intrachain linked but uncross-linked hemoglobin for the benzene tricarboxyl modified hemoglobin, $\alpha_2(\beta_{82}{}^1$>X$)_2$, was found to be 10.8 mm Hg compared to between 9.4 and 10.2 for the analogous isophthaloyl modified hemoglobin.

Figure 14:
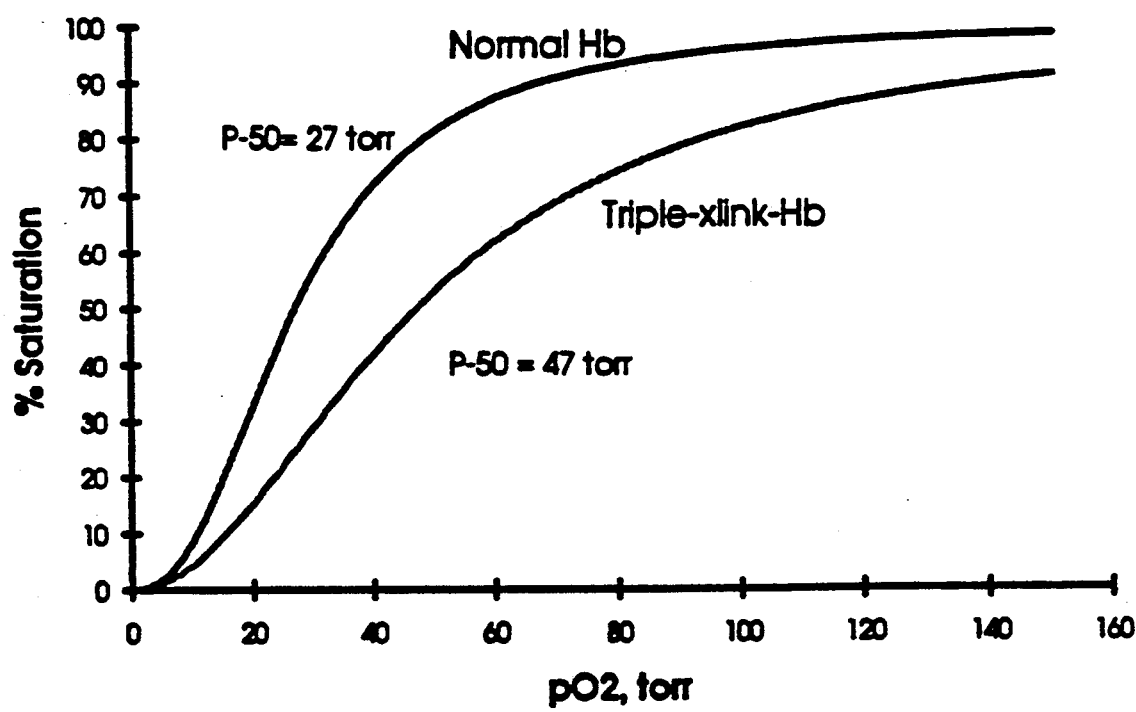
FIG. 14 is an oxygen binding curve showing the percent saturation of oxygen as a function of the partial pressure of oxygen, for both normal hemoglobin and a modified hemoglobin of the invention cross-linked with 1,3,5-benzene tricarboxylic acid tris(methyl phosphate)

The triligand modified hemoglobin, $\alpha_2\beta_{82}{}^1$>X82$\beta$, exhibits a markedly sigmoid oxygen binding curve as shown in FIG. 14. The $P_{50}$ of this preparation at 37° C. and pH 7.4 is about 47 mm Hg. Because of the strong cooperative properties, it should be an excellent oxygen transporter.

Figure 15:
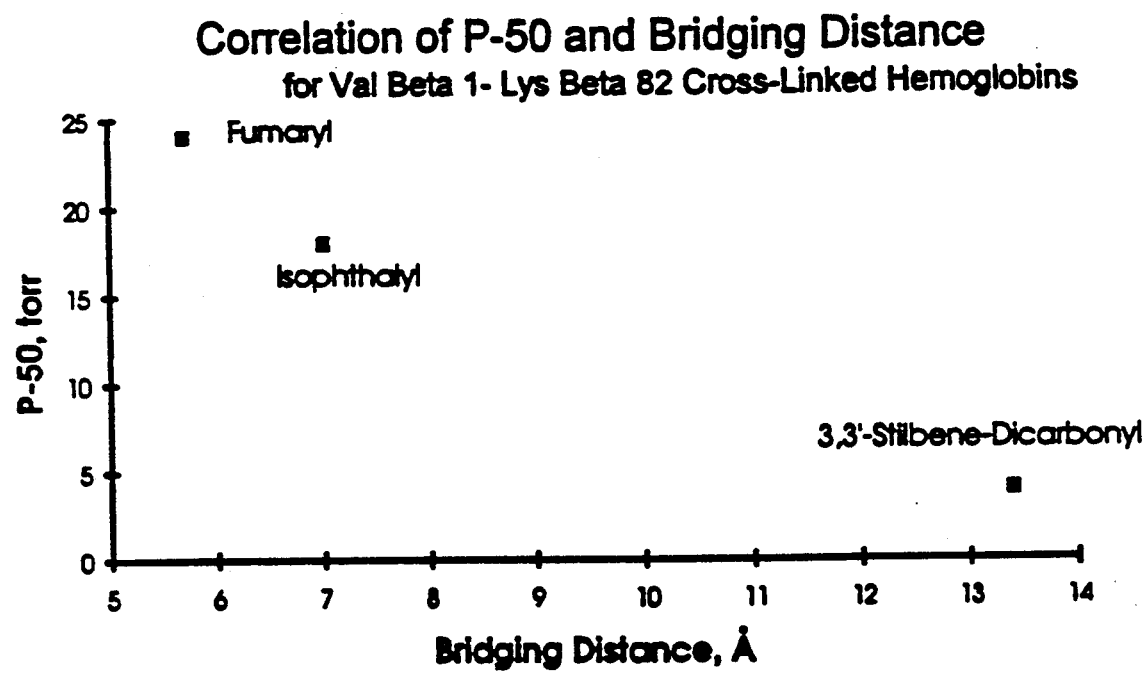
FIG. 15 shows the correlation of $P_{50}$ and bridging distances for $\beta 1\text{-}X\text{-}82\beta$ cross-linked hemoglobins.

Interestingly, a direct correlation can be made between the $P_{50}$ of the modified hemoglobin and the bridging distance of the $\beta$1-X-82$\beta$ cross-link. FIG. 15 shows that $P_{50}$ decreases with increasing length of the cross-link from 5 to 14 angstroms. It may thus be possible to provide modified hemoglobins of a specified $P_{50}$ by selecting a specific cross-linking reagent of the appropriate size.

EXAMPLE 3

Figure 16:
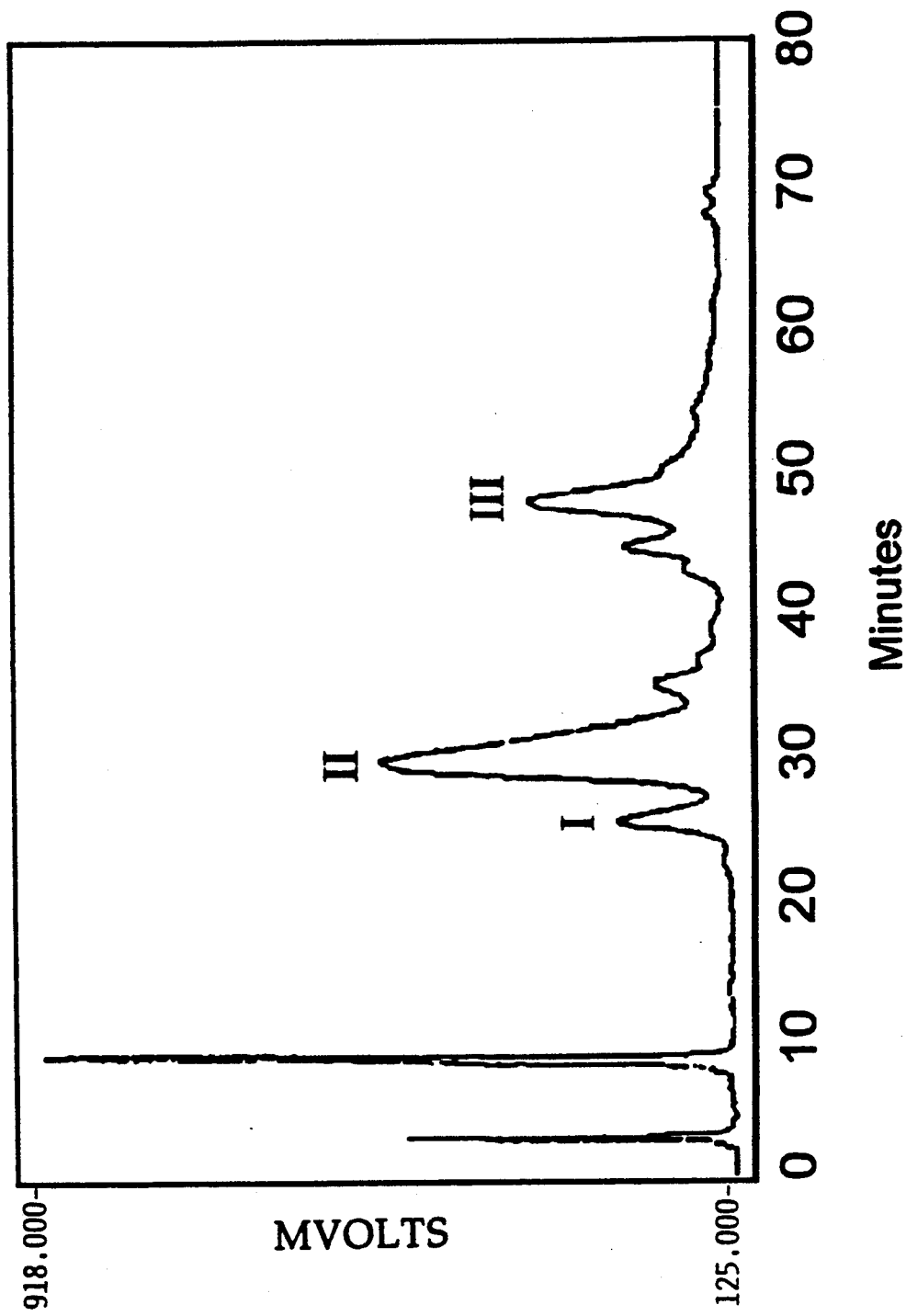
FIG. 16 shows the globin chain separation of 1,3,5-benzene tricarboxylic acid tris (methyl phosphate) treated carbonmonoxyhemoglobin.

Carbonmonoxyhemoglobin was modified with 1,3,5-benzene tricarboxylic acid tris (methyl phosphate) using the procedure described above for deoxyhemglobin except that the process was not carried out under nitrogen. The products of carbonmonoxyhemoglobin modified with 1,3,5-benzene tricarboxylic acid tris (methyl phosphate) were analyzed by reversed phase HPLC on preparative size Synchropak AX 300 anion exchange column. The modified hemoglobins were further purified by rechromatography on a preparative size CM 300 cation exchange column. Zones from cation exchange rechromatography were then subjected to globin chain separation using Vydak C-4 large pore reversed phase columns. The results of globin chain separation are shown in FIG. 16.

Figure 17:
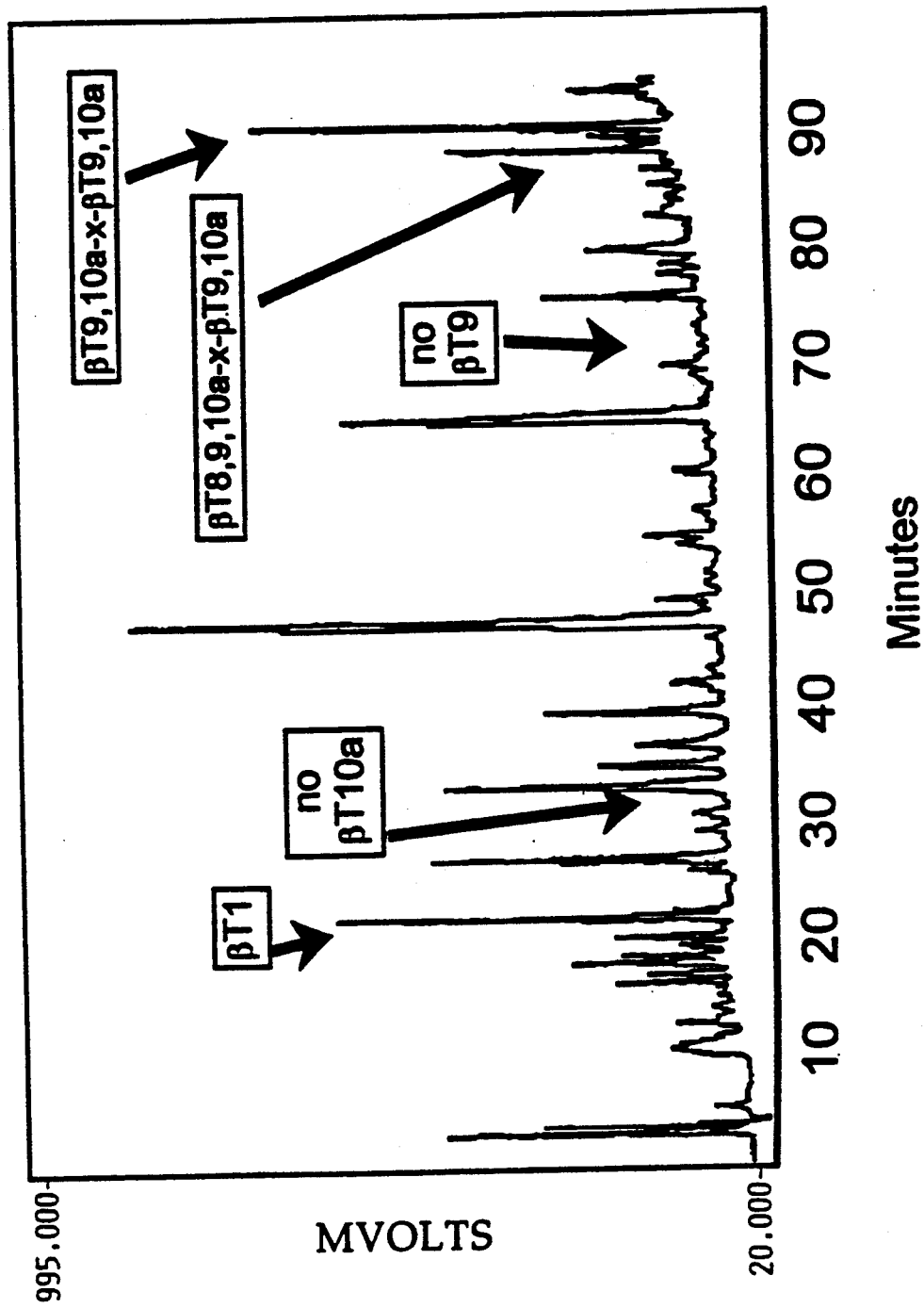
FIG. 17 shows the peptide pattern of modified globin $\beta 82\text{-}X\text{-}82\beta$ from carbonmonoxyhemoglobin modified with 1,3,5-benzene tricarboxylic acid tris (methyl phosphate)

The globin chains were isolated, treated by oxidations or aminoethylation to stabilize the cysteinyl residues, hydrolyzed with trypsin and glu-C proteinase and the resultant peptides were analyzed. FIG. 17 shows analytical profiles of the peptides derived from zone III. Zone III is one of the main reaction products and is cross-linked between the $\beta$82-lysine of one chain and the $\beta$82 lysine of the other chain. The cross-linked peptide appears as two peaks due to incomplete hydrolysis of a lysyl residue corresponding to $\beta$T8.

EXAMPLE 4

Carbonmonoxyhemoglobin was modified with isophthaloyl bis (methyl phosphate), fumaryl bis(methyl phosphate), and 3,3'-stilbene dicarboxylic acid bis (methyl phosphate) as described in Example 3. 5 ml of human carbonmonoxyhemoglobin and 0.5 ml of 1.0M bis-tris-HCl buffer (pH 7.2) was reacted with 2-3 ml of a buffered solution of reagent in a rotary reaction vessel at 40°-60° C. The amount of the cross-linker and the buffer gave a final concentration after the injection of the cross-linker of 1 mM in hemoglobin and 0.1M in buffer. Three equivalents of the cross-linker were injected.

The products of carbonmonoxyhemoglobin modified with the compounds were analyzed by anion exchange HPLC on preparative size Synchropak AX 300 anion exchange column, tryptic digests and peptide and amino acid analysis.

Figure 18:
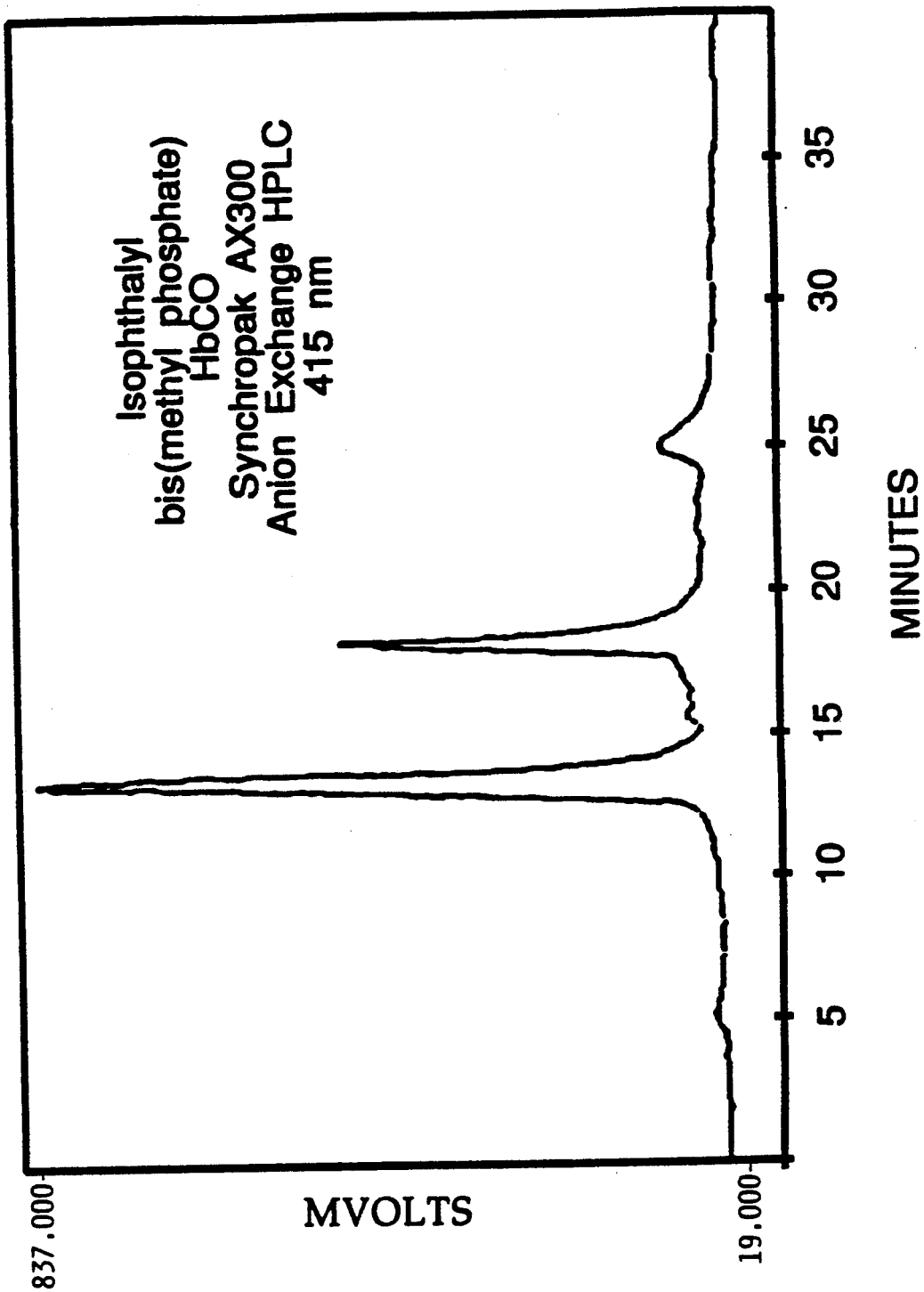
FIG. 18 shows an anion exchange chromatogram of the reaction products resulting from the treatment of carbonmonoxyhemoglobin with isophthaloyl bis (methyl phosphate).

FIG. 18 shows an anion exchange chromatogram of the reaction products resulting from the treatment of carbonmonoxyhemoglobin with isophthaloyl bis(methyl phosphate).

Figure 19:
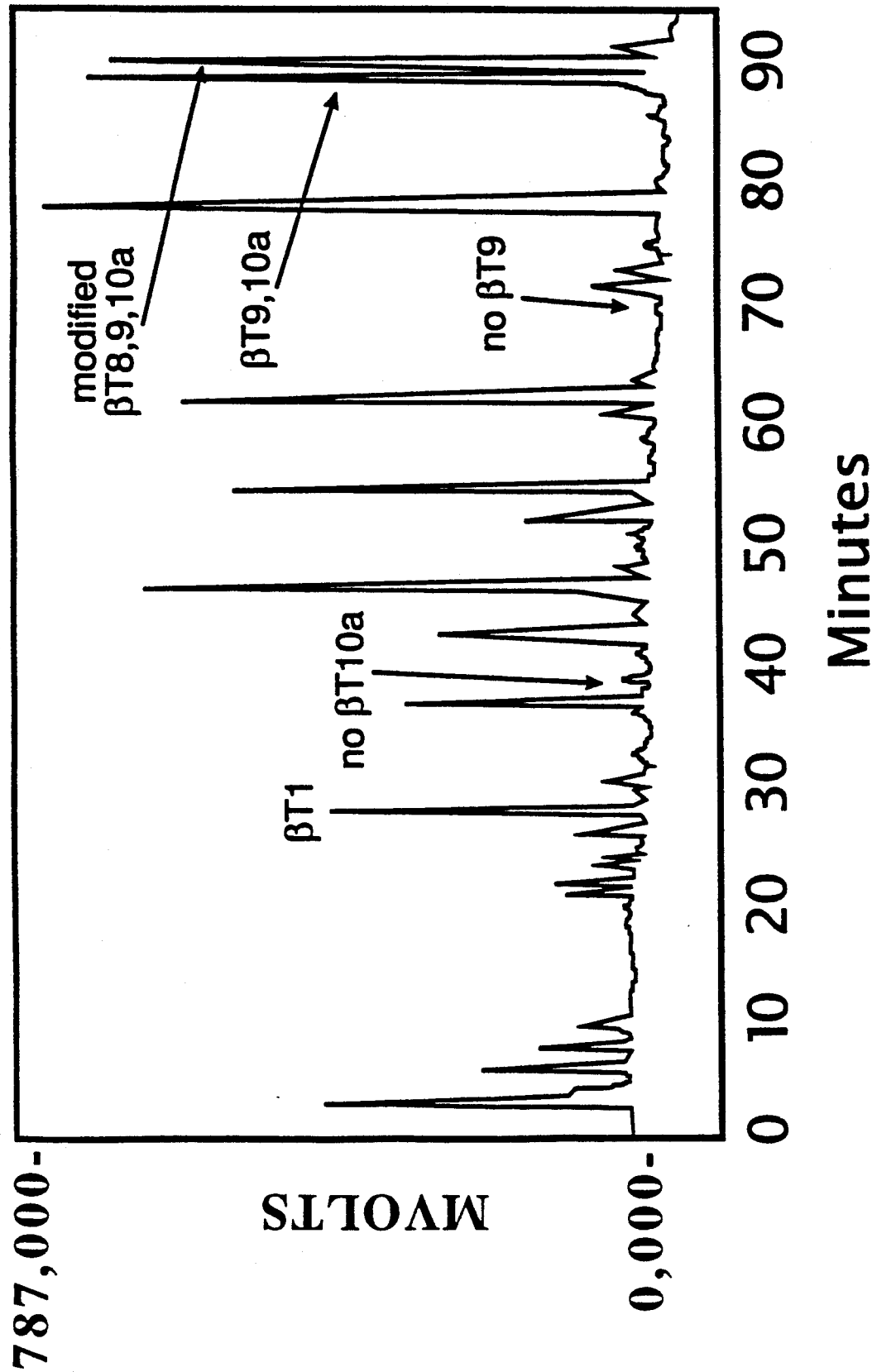
FIG. 19 shows the peptide pattern of zone 6 from the globin chain separation of the 3,3'-stilbene dicarboxylic acid bis (methyl phosphate) treated deoxyhemoglobin.

FIG. 19 shows a reversed phase HPLC chromatogram of zone 6 from the globin chain separation of deoxyhemoglobin modified with 3,3'-stilbene dicarboxylic acid bis (methyl phosphate). Zone 6 corresponds to the $\beta$-82-$\beta$82 cross-linked peptides. The sites of modifications and structure of the modified hemoglobins could be determined since acylation by the stilbene reagent prevented tryptic cleavage at the modified lysine. This resulted in the appearance of peptides not found in the digest of normal hemoglobin. Further hydrolysis with Glu-C-Endoproteinase assured that the product was not an artifact. Since stilbene absorbs in the ultraviolet wavelength (306 nm) it could be accurately quantitated in the new peptide. In the case of the $\beta$82-$\beta$82' cross-linked material, all $\beta$T-9 and $\beta$T-10a peptides were absent. Polyacrylamide gel electrophoresis (PAGE) in the presence of sodium dodecyl sulfate separated peptides by molecular weight and dissociated subunits. Analysis of the modified hemoglobin identified as having β82-β82' link by PAGE showed uncoupled α subunits and dimeric β subunits.

Table V shows the structure of the deoxy- and carbonmonoxy- major components of the hemoglobin modified with isophthaloyl bis (methyl phosphate, fumaryl bis(methyl phosphate), 3,3' stilbene bis (methyl phosphate). The primary product of the reaction of carbonmonoxyhemoglobin with 3,3'-trans-stilbenedicarboxylic acid bis (methyl phosphate) is cross-linked between the epsilon amino group of lysine-82 of each beta chain by a trans stilbene diacid group. The oxygen affinity of this modified hemoglobin is approximately the same as that of human hemoglobin within the erythrocyte and full cooperativity is maintained. The $P_{50}$ of the modified hemoglobin is 10 under the following conditions: 50 mM bis Tris, 0.1M Cl$^-$, pH 7.4, 25° C., 55 μm heme. Since position 1 is not modified it is expected that full carbon dioxide carrying capacity will be maintained. Table V also shows the structure of the major components of deoxyhemoglobin with 2,3 DPG, modified with the reagents.

of 75% cross-linked material was obtained. The main product was triply cross-linked from beta-1-lys-82 to beta-2-val-1 and beta-2-lys-82. The modified hemoglobin has a low oxygen affinity ($P_{50}=17.9$ mm Hg, conditions 50 mM bis-Tris, 0.1M Cl$^-$, pH 7.4, 25° C. 55 μm heme) and good cooperativity (Hill coefficient, 2.4). Other products were singly cross-linked between β-1-lys-82 and β-2-val-1.

TABLE I

DISTANCES BETWEEN β1Val—NH$_2$ AND β82Lys—NH$_2$ IN OXY- & DEOXY-Hb

| Residues | Distances Å | |
|---|---|---|
| | Deoxy- | Oxy- |
| β$_1$1Val—β$_2$1Val | 18.4 | 19.9 |
| β$_1$1Val—β$_2$82Lys | 11.5 | 15.5 |
| β$_1$82Lys—β$_2$82Lys | 9.3 | 10.7 |
| β$_1$1Val—β$_1$82Lys | 9.9 | 5.4 |

BRIDGING DISTANCES FOR SELECTED CROSS-LINKERS

| Cross-linker | Distances Å |
|---|---|
| Fumaryl | 6.1 |
| Isophthalyl | 7.3 |
| Terephthalyl | 7.5 |
| 3,3'-Stilbene | 13.2 |
| DIDS | 16 |

EXAMPLE 5

TABLE II

FUNCTIONAL PROPERTIES OF MODIFIED HEMOGLOBINS

| | $P_{50}$ ($n_{50}$) | | | 1,3,5-benzene Tricarboxyl | Cyclohexane |
|---|---|---|---|---|---|
| | Fumaryl | Isophthalyl | 3,3'-Silbene | | |
| α$_2$(β1-X)$_2$ | | 6.6 (2.0) | | | |
| α$_2$(β82-X)$_2$ | 9.8 (2.3) | 8.7 (2.8) | 3.1 (2.3) | | 14.4 (−2.2) |
| | | | 3.4 (2.1) | | 16 (2.3)* |
| | | | 6.8 (2.4)* | | |
| α$_2$β82-X-82β | 3.1 ( ) | | 9.3 biphasic | | 16 (~2.1) |
| | | | 9.8 biphasic | | |
| | | | 10.0 (2.8) | | |
| | | | 9.8 (2.7) | | |
| α$_2$β1-X-144β | | | 2.4 biphasic** | | |
| α$_2$β1-X-82β | 24 (2.2) | 17.0 (2.3) | 4.2 (2.5) | | 18.1 (1.9)* |
| | | 17.8 (2.7) | 3.4 (2.6) | | |
| | | | 3.3 (2.4) | | |
| α$_2$(β$_{82}^1$ > X)$_2$ | 8.2 (2.0) | 9.4 (2.6) | | 10.8 (2.3) | |
| | | 10.2 (2.1) | | | |
| α$_2$β82-X-1β82-X | | | 4.7 (2.0) | 17.0 biphasic | |
| α$_2$β$_{82}^1$ > X-82β | | | | 17.9 (2.3) | 16.6 (1.7) |
| α$_2$β$_{82}^1$ > X-82β1-X | | | | | 28 biphasic |
| α$_2$β$_{82-X-1\beta}^{1-X-82}$β | 22.5 biphasic | | | | |

Conditions: 50 mM bis Tris, 0.1 M Cl$^-$, pH 7.4, 25° C., 55 μM Heme
Normal Unmodified Hb A: $P_{50}$ = 4.9, $n_{50}$ = 2.9
*A methyl phosphate may be on these modified hemoglobins.

Deoxyhemoglobin was modified by infusion reaction with 1,3,5-benzene tricarboxyl tris (methyl phosphate). 5 ml of deoxyhemglobin and 0.5 ml of 1M bis-tris-HCl buffer at pH 7.2 in a rotary reaction apparatus under nitrogen was treated with approximately 2-3 ml of the buffered solution of 1,3,5-benzene tricarboxyl tris (methyl phosphate) at 60° C. The quantity of the cross-linker and the buffer is such that the final concentrations after the injection of all the solution of the cross-linker are 1 mM in hemoglobin and 0.1M in buffer. Three equivalents of the cross-linker were injected. The reagent was added by syringe pump (reagent at room temperature) during one hour and further reacted for one hour at 60° C. After reaction, cooled product was converted to the carbonmonoxy form and analyzed by HPLC, tryptic digest and amino acid analysis. A yield

TABLE III

| Actual peak | intensity | Pred. peak | Charge | Compound mass |
|---|---|---|---|---|
| 1140.60 | 23,019 | 1140.25 | 28 | 31,908.58 |
| 1182.80 | 35,546 | 1182.45 | 27 | 31,908.39 |
| 1277.00 | 85,531 | 1276.95 | 25 | 31,899.80 |
| 1330.60 | 118,585 | 1330.13 | 24 | 31,910.21 |
| 1388.00 | 134,750 | 1387.91 | 23 | 31,900.82 |
| 1460.80 | 121,733 | 1450.95 | 22 | 31,895.43 |
| 1520.00 | 93,182 | 1520.00 | 21 | 31898.83 |
| 1596.00 | 60,860 | 1595.95 | 20 | 31,899.84 |
| 1680.20 | 43,877 | 1679.89 | 19 | 31,904.65 |
| 1773.20 | 24,788 | 1773.17 | 18 | 31,899.46 |

Avg. compound mass 31,902.60
Std. Deviation: 5.01
10 Estimates of compoun mass

TABLE IV

Isophthaloyl Modified Hemoglobins

| Globin Zone | Modification | Cross-linkage |
|---|---|---|
| IV | $\beta_1 82Lys—I$; $\beta_2 82Lys—I$ | None |
| VI | $\beta_1 1Val—I—Lys82\beta_2$ | Single |
| V | $\beta_1 1Val—I—Lys82\beta_2$ <br> $\beta_1 82Lys—I—Val1\beta_2$ | Double |

TABLE V

STRUCTURE OF MODIFIED GLOBINS OF MAJOR HEMOGLOBIN COMPONENTS

| Fumaryl | Isophthalyl | 3,3'Stilbenedicarbonyl |
|---|---|---|
| DeoxyHb | | |
| $\oplus 1$-F-$82\beta$ | $\beta 1$-I-$82\beta$ | $\beta 1$-S-$82\beta$ |
| $\beta_{82}{}^1 > F$ | $\beta_{82}{}^1 > F$ | — |
| — | — | $\beta 82$-S-$1\beta 82$-S |
| $\beta 82$-F | $\beta 82$-I | $\beta 82$-S |
| — | — | $\beta 82$-S-$82\beta$ |
| $\alpha 99$-F-$99X$ | $\alpha 99$-I-$99\alpha$ | — |
| COHb | | |
| $\beta 82$-F-$82\beta$ | $\beta 82$-I-$82\beta$ | $\beta 82$-S-$82\beta$ |
| $\beta 82$-F | $\beta 82$-I | $\beta 82$-S |
| DeoxyHb with 2,3 DPG | | |
| $\alpha 99$-F-$99\alpha$ | $\alpha 99$-I-$99\alpha$ | No $\alpha$ Hbs produced |
| $\alpha 1$-F-$139\alpha$ | $\alpha 99$-I-$139\alpha$ | |
| $\alpha 1$-F | $\alpha 1$-I | |

We claim:

1. A modified hemoglobin comprising hemoglobin which is intramolecularly cross-linked between the epsilon amino group lysine 82 of a first $\beta$ chain of the hemoglobin and the alpha amino group valine-1 of a second $\beta$ chain of the hemoglobin, which has a distance between the $\beta$ chains at the cross-link between about 5 to 9 angstroms, and which is obtained by cross-linking hemoglobin with a cross-linking reagent comprising an aromatic- or aliphatic-derived acyl material having at least two anionic leaving groups each anionic leaving group being adjacent to an electrophile group, said cross-linking reagent being selected such that a first electrophile group reacts covalently with the epsilon amino group lysine 82 of a first $\beta$ chain of said hemoglobin and a second electrophile group reacts covalently with the alpha amino group valine-1 of a second $\beta$ chain of said hemoglobin.

2. The modified hemoglobin as claimed in claim 1 which is additionally covalently cross-linked with the epsilon amino group lysine 82 of the second $\beta$ chain of said hemoglobin or the alpha amino group valine-1 of the first $\beta$ chain of the hemoglobin and wherein the cross-linking reagent comprises an aromatic- or aliphatic-derived acyl material having at least three anionic leaving groups and wherein a third electrophile group reacts covalently with the epsilon amino group lysine 82 of said second $\beta$ chain of said hemoglobin or the alpha amino group valine-1 of said first $\beta$ chain of said hemoglobin.

3. The modified hemoglobin as claimed in claim 2 wherein the third electrophile group reacts covalently with the epsilon amino group lysine 82 of said second $\beta$ chain of said hemoglobin.

4. The modified hemoglobin as claimed in claim 2 wherein the third electrophile group reacts covalently with the alpha amino group valine-1 of said first $\beta$ chain of said hemoglobin.

5. The modified hemoglobin as claim in claim 3 which is additionally covalently cross-linked with the alpha amino group valine-1 of the first $\beta$ chain of said hemoglobin and wherein the cross-linking reagent comprises an aromatic- or aliphatic-derived acyl material having at least four anionic leaving groups and wherein a fourth electrophile group reacts covalently with the alpha amino group valine-1 of said first $\beta$ chain of said hemoglobin.

6. The modified hemoglobin as claimed in claim 4 which is additionally covalently cross-linked with the epsilon amino group lysine 82 of the second $\beta$ chain of said hemoglobin and wherein the cross-linking reagent comprises an aromatic- or aliphatic-derived acyl material having at least four anionic leaving groups and wherein a fourth electrophile group reacts covalently with the epsilon amino group lysine 82 of said second $\beta$ chain of said hemoglobin.

7. The modified hemoglobin as claimed in claim 1 wherein the cross-linking reagent is a compound of the formula I:

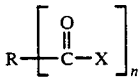

wherein R is a linear or branched alkyl, alkenyl, phenyl, diphenylalkenyl, benzyl, naphthyl, phenylalkyl, phenylalkenyl or diphenylalkyl; X is an anionic leaving group; and n is an integer.

8. The modified hemoglobin as claimed in claim 7 wherein n is an integer between 2 and 4.

9. The modified hemoglobin as claimed in claim 7, wherein X is a phosphate, alkanesulfonate, alkylsulfate, asalicylate or hydroxyl.

10. The modified hemoglobin as claimed in claim 7, wherein X has the formula II.

wherein one of $R^1$ and $R^2$ is $—O^-$ and the other of $R^1$ and $R^2$ represents a linear or branched akyl group having up to 4 carbon atoms, benzyl or phenyl.

11. The hemoglobin as claimed in claim 7, wherein R is phenyl.

12. The hemoglobin as claimed in claim 7 wherein n is 3.

13. The hemoglobin as claimed in claim 10, wherein the cross-linking reagent is the tris acyl (methyl phosphate) ester of 1,3,5-benzene-tricarboxylic acid or isophthalic bis (methyl phosphate).

14. The hemoglobin as claimed in claim 10, wherein the cross-linking reagent is the tris dibromo salicylate of 1,3,5-benzene-tricarboxylic acid or the dibromosalicylate of isophthalic acid.

15. The modified hemoglobin as claimed in claim 1 having oxygen affinities in the physiologically useful range.

16. A method of preparing a modified hemoglobin comprising (a) reacting hemoglobin with a cross-linking reagent for a sufficient time and under suitable conditions to yield a cross-linked hemoglobin said cross-linking reagent comprising an aromatic- or aliphatic-derived acyl material having at least two anionic leaving groups each anionic leaving group being adjacent to an electrophile group, sand said cross-linking reagent being selected such that a first electrophile group reacts covalently with the epsilon amino group lysine 82 of a first β chain of said hemoglobin and a second electrophile group reacts covalently with the alpha amino group valine-1 of a second β chain of said modified hemoglobin whereby said hemoglobin is intramolecularly cross-linked between said beta chains such at the distance between the β chains at said cross-link is between about 5 to 9 angstroms; and (b) purifying the resulting cross-linked hemoglobin.

17. The modified hemoglobin as claimed in claim 1 or obtained as claimed in claim 16, wherein said hemoglobin is deoxyhemoglobin, carbonmonoxyhemoglobin or oxyhemoglobin.

18. The modified hemoglobin as claimed in claim 1 or obtained as claimed in claim 16, wherein said hemoglobin is selected from the group consisting of human, equine, porcine, ovine, bovine, simian and fish hemoglobin.

19. The modified hemoglobin as claimed in claim 1 wherein the cross-linking reagent is a compound of the following formula:

$$R[-R^1-X]_n \qquad I$$

wherein R is a linear or branched alkyl, alkenyl, phenyl, diphenylalkenyl, benzyl, naphthyl, phenylalkyl, phenylalkenyl or diphenylalkyl; $R^1$ is an electrophile group, X is an anionic leaving group; and n is an integer.

20. The modified hemoglobin as claimed in claim 19 wherein n is an integer between 2 and 4.

21. The modified hemoglobin as claimed in claim 19, wherein X is a phosphate, alkanesulfonate, alkylsulfate, salicylate, or hydroxyl.

22. The method as claimed in claim 16 wherein the cross-linking reagent comprises an aromatic- or aliphatic-derived acyl material having at least three anionic leaving groups and wherein a third electrophile group covalently reacts with the epsilon amino group lysine 82 of said second β chain of the hemoglobin or the alpha amino group valine-1 of said first β chain of the hemoglobin.

23. The method as claimed in claim 22 wherein the third electrophile group reacts covalently with the epsilon amino group lysine 82 of said second β chain of said hemoglobin.

24. The method as claimed in claim 22 wherein the third electrophile group reacts covalently with the alpha amino group valine-1 of said first β chain of the hemoglobin.

25. The method as claimed in claim 23 wherein the cross-linking reagent comprises an aromatic- or aliphatic-derived acyl material having at least four anionic leaving groups and wherein a fourth electrophile group covalently reacts with the alpha amino group valine-1 of said first β chain of said hemoglobin.

26. The method as claimed in claim 24 wherein the cross-linking reagent comprises an aromatic- or aliphatic-derived acyl material having at least four anionic leaving groups and wherein a fourth electrophile group covalently reacts with the epsilon amino group lysine 82 of the second β chain of the hemoglobin.

27. The method as claimed in claim 16 wherein the cross-linking reagent is a compound of the following formula:

$$R[-R^1-X]_n$$

wherein R is a linear or branched alkyl, alkenyl, phenyl, diphenylalkenyl, benzyl, naphthyl, phenylalkyl, phenylalkenyl or diphenylalkyl; $R^1$ is an electrophile group, X is an anionic leaving group; and n is an integer.

28. The method as claimed in claim 16 wherein the cross-linking reagent is a compound of the formula I:

$$R\left[-\underset{\underset{\parallel}{O}}{C}-X\right]_n \qquad I$$

wherein R is a linear or branched alkyl, alkenyl, phenyl, diphenylalkenyl, benzyl, naphthyl, phenylalkyl, phenylalkenyl or diphenylalkyl; X is an anionic leaving group; and n is an integer.

29. The method as claimed in claim 27 or 28, wherein n is an integer between 2 and 4.

30. The method as claimed in 27 or 28, wherein X is a phosphate, alkanesulfonate, alkylsulfate, salicylate, or hydroxyl.

31. The method as claimed in claim 27 or 28, wherein X has the formula II $$\underset{\underset{\mid}{R^2}}{\overset{\underset{\parallel}{O}}{O-P-R^1}} \qquad II$$

wherein one of $R^1$ and $R^2$ are —O— and the other of $R^1$ and $R^2$ represents a linear or branched alkyl group having up to 4 carbon atoms, benyl or phenyl.

32. The method as claimed in claim 27 or 28, wherein R is phenyl.

33. The method as claimed in claim 27 or 28 wherein n is 3.

34. The method as claimed in claim 16, wherein the cross-linking reagent is the tris tris (methyl phosphate) ester of 1,3,5-benzene-tricarboxylic acid or isophthalic bis (methyl phosphate).

35. The method as claimed in claim 16, wherein the cross-linking reagent is the tris dibrom salicylate of 1,3,5-benzene-tricarboxylic acid or the dibromosalicylate of isophthalic acid.

36. The method as claimed in claim 16, wherein the ratio of cross-linking reagent to hemoglobin is 2:1 to 10:1M, and the cross-linking is carried out at a temperature of from 20° C. to 60° C., a pH of from 6 to 8, and a reaction time of up to 3 days at room temperature or 3 hours at 60° C.

* * * * *